(12) United States Patent
Nair

(10) Patent No.: US 8,545,927 B2
(45) Date of Patent: Oct. 1, 2013

(54) LACTOFERRIN-BASED BIOMATERIALS FOR TISSUE REGENERATION AND DRUG DELIVERY

(75) Inventor: Lakshmi Sreedharan Nair, Avon, CT (US)

(73) Assignee: University of Connecticut, Farmington, CT (US)

( * ) Notice: Subject to any disclaimer, the term of this patent is extended or adjusted under 35 U.S.C. 154(b) by 209 days.

(21) Appl. No.: 13/104,653

(22) Filed: May 10, 2011

(65) Prior Publication Data

US 2012/0122767 A1  May 17, 2012

Related U.S. Application Data

(60) Provisional application No. 61/332,935, filed on May 10, 2010.

(51) Int. Cl.
*A61K 38/40* (2006.01)
*A61K 47/42* (2006.01)

(52) U.S. Cl.
USPC .......... 427/2.26; 424/426; 424/484; 435/182; 514/16.7; 514/17.1; 623/23.57; 623/926

(58) Field of Classification Search
None
See application file for complete search history.

(56) References Cited

U.S. PATENT DOCUMENTS

| | | | |
|---|---|---|---|
| 4,097,935 A | 7/1978 | Jarcho | |
| 4,131,597 A | 12/1978 | Bluethgen et al. | |
| 4,192,021 A | 3/1980 | Deibig et al. | |
| 4,223,412 A | 9/1980 | Aoyagi et al. | |
| 4,356,572 A | 11/1982 | Guillemin et al. | |
| 4,629,464 A | 12/1986 | Takata et al. | |
| 4,655,777 A | 4/1987 | Dunn et al. | |
| 4,698,375 A | 10/1987 | Dorman et al. | |
| 4,842,604 A | 6/1989 | Dorman et al. | |
| 5,032,129 A | 7/1991 | Kurze et al. | |
| 5,266,476 A | 11/1993 | Sussman et al. | |
| 5,514,181 A | 5/1996 | Light et al. | |
| 5,516,697 A * | 5/1996 | Kruzel | 436/84 |
| 5,543,209 A | 8/1996 | Duquet et al. | |
| 5,595,621 A | 1/1997 | Light et al. | |
| 5,626,861 A | 5/1997 | Laurencin et al. | |
| 5,629,009 A | 5/1997 | Laurencin et al. | |
| 5,755,809 A | 5/1998 | Cohen et al. | |
| 5,766,618 A | 6/1998 | Laurencin et al. | |
| 5,866,155 A | 2/1999 | Laurencin et al. | |
| 5,935,168 A * | 8/1999 | Yang et al. | 623/11.11 |
| 6,017,366 A | 1/2000 | Berman | |
| 6,120,789 A | 9/2000 | Dunn et al. | |
| 6,136,029 A | 10/2000 | Johnson et al. | |
| 6,228,111 B1 | 5/2001 | Törmälä | |
| 6,308,509 B1 | 10/2001 | Scardino et al. | |
| 6,333,311 B1 | 12/2001 | Nuijens et al. | |
| 6,451,059 B1 | 9/2002 | Janas et al. | |
| 6,592,814 B2 | 7/2003 | Wilcox et al. | |
| 6,122,057 B2 | 10/2006 | Beam et al. | |
| 7,163,557 B2 | 1/2007 | D'Eredità | |
| 7,235,295 B2 | 6/2007 | Laurencin et al. | |
| 7,241,486 B2 | 7/2007 | Pirhonen | |
| 7,250,550 B2 | 7/2007 | Overby et al. | |
| 7,323,442 B2 | 1/2008 | Yajima et al. | |
| 7,351,262 B2 | 4/2008 | Bindseil et al. | |
| 7,524,814 B2 | 4/2009 | Engelmayer et al. | |
| 2002/0111295 A1 | 8/2002 | Yajima et al. | |
| 2003/0191193 A1 | 10/2003 | Cornish et al. | |
| 2004/0191292 A1 | 9/2004 | Chou | |
| 2005/0100581 A1 | 5/2005 | Laurencin et al. | |
| 2005/0169882 A1 | 8/2005 | Lowe et al. | |
| 2006/0229246 A1 | 10/2006 | Hawley-Nelson et al. | |
| 2006/0263417 A1 | 11/2006 | Lelkes et al. | |
| 2007/0061015 A1 | 3/2007 | Jensen et al. | |
| 2007/0077267 A1 | 4/2007 | Molz, IV et al. | |
| 2007/0083268 A1 | 4/2007 | Teoh et al. | |
| 2007/0269481 A1 | 11/2007 | Li et al. | |
| 2007/0275871 A1 | 11/2007 | Sadeghi et al. | |
| 2008/0188644 A1 | 8/2008 | Cornish et al. | |
| 2008/0220042 A1 | 9/2008 | Hashi et al. | |
| 2008/0249638 A1 | 10/2008 | Asgari | |
| 2009/0028921 A1 | 1/2009 | Arinzeh | |
| 2009/0061152 A1 | 3/2009 | DeSimone et al. | |
| 2009/0068244 A1 | 3/2009 | Weber et al. | |

(Continued)

FOREIGN PATENT DOCUMENTS

| | | |
|---|---|---|
| EP | 0 426 924 A1 | 11/1989 |
| EP | 1 426 066 A1 | 6/2004 |

(Continued)

OTHER PUBLICATIONS

Naot et al. lactoferrin—A Novel Bone Growth Factor. Clinical Medicine & Research. 2005, vol. 3, No. 2, pp. 93-101.*

Abarrategi, A., et al., "Multiwall Carbon Nanotube Scaffolds for Tissue Engineering Purposes," *Biomaterials* 29:94-102 (2008).

Armentano, I., et al. "Effects of carbon nanotubes (CNTs) on the processing and in-vitro degradation of poly (DL-lactide-*co*-glycolide)/CNT films," *J Mater Sci: Mater Med* 19:2377-2387 (2008).

Barnes, C.P., et al., "Nanofiber Technology: Designing the Next Generation of Tissue Engineering Scaffolds," *Advanced Drug Delivery Reviews* 59:1413-1433 (2007).

(Continued)

*Primary Examiner* — Jeffrey E Russel

(74) *Attorney, Agent, or Firm* — Hamilton, Brook, Smith & Reynolds, P.C.

(57) ABSTRACT

The invention provides biomatrix compositions comprising cross-linked lactoferrin, either alone or in combination with other organic or inorganic components. Also provided are methods of making and using the biomatrix compositions. As described herein, cross-linked lactoferrin biomatrix retains the bioactivities of the lactoferrin molecule. The biomatrix composition can act as a matrix for cell adhesion and growth and is particularly useful in musculoskeletal tissue regeneration. The biomatrix compositions can be pre-formed or injectable and can act as a cell, drug or protein delivery vehicle.

30 Claims, 19 Drawing Sheets

(19 of 19 Drawing Sheet(s) Filed in Color)

(56) References Cited

U.S. PATENT DOCUMENTS

| | | | |
|---|---|---|---|
| 2009/0130191 A1 | 5/2009 | Ishikado et al. | |
| 2009/0169594 A1 | 7/2009 | Polizu et al. | |
| 2009/0253627 A1 | 10/2009 | Engelmayer et al. | |
| 2009/0259025 A1 | 10/2009 | Cornish et al. | |
| 2009/0281029 A1 | 11/2009 | Nojima et al. | |
| 2010/0075904 A1 | 3/2010 | Laurencin et al. | |
| 2010/0087851 A1* | 4/2010 | Jones et al. | 606/213 |
| 2010/0310623 A1 | 12/2010 | Laurencin et al. | |

FOREIGN PATENT DOCUMENTS

| | | |
|---|---|---|
| WO | WO 2008/100534 A2 | 8/2008 |
| WO | WO 2009123720 A2 * | 10/2009 |
| WO | WO 2010/141718 A1 | 12/2010 |

OTHER PUBLICATIONS

Boonsongrit, Y., et al., "Controlled Release of Bovine Serum Albumin From Hydroxyapatite Microspheres for Protein Delivery System," *Materials Science and Engineering B* 148:162-165 (2008).

Borden, M., et al., "Structural and Human Cellular Assessment of a Novel Microsphere-based Tissue Engineered Scaffold for Bone Repair," *Biomaterials* 24:597-609 (2003).

Borden, M., et al., "The Sintered Microsphere Matrix for Bone Tissue Engineering: In Vitro ostcoconductivity Studies," *J Biomed Mater Res* 61:421-429 (2002).

Borden, M., et al., "Tissue Engineered Microsphere-based Matrices for Bone Repair: Design and Evaluation," *Biomaterials* 23:551-559 (2002).

Boyan, B.D., et al., "Mechanisms Involved in Osteoblast Response to Implant Surface Morphology," *Annu. Rev. Mater. Res.* 31:357-371 (2001).

Boyan, B.D., et al., "Role of Material Surfaces in Regulating Bone and Cartilage Cell Response," *Biomaterials* 17:137-146 (1996).

Cai, K., et al., "Surface Modification of titanium Thin Film With Chitosan via Electrostatic Self-Assembly Technique and its Influence on Osteoblast Growth Behavior," *J Mater Sci: Mater Med* 19:499-506 (2008).

Chen, G.-X., et al., "Controlled Functionalization of Multiwalled Carbon Nanotubes with Various Molecular-Weight Poly(L-lactic acid)," *J. Phys. Chem. B* 109:22237-22243 (2005).

Chlopek, J., et al., "In Vitro Studies of Carbon Nanotubes Biocompatibility," *Carbon* 44:1106-1111 (2006).

Correa-Duarte, M.A., et al., Fabrication and Biocompatibility of Carbon Nanotube-Based 3D Networks as Scaffolds for Cell Seeding and Growth, *Nano Letters* 4(11):2233-2236 (2004).

Cuddihy, M.J. and Kotov, N.A., "Poly(lactic-co-glycolic acid) Bone Scaffolds with Inverted Colloidal Crystal Geometry," *Tissue Engineering: Part A* 14(10):1639-1649 (2008).

Descamps, M., et al., "Manufacture of Macroporous β-Tricalcium Phosphate Bioceramics," *Journal of the European Ceramic Society* 28:149-157 (2008).

Devin, J.E., et al., "Three-Dimensional Degradable Porous Polymer-Ceramic Matrices for Use in Bone Repair," *J. Biomater. Sci. Polymer Edn*, 7(8):661-669 (1996).

Edwards, S.L., et al., "Tubular micro-scale multiwalled carbon nanotube-based scaffolds for tissue engineering," *Biomaterials* 30:1725-1731 (2009).

Erisken, C., et al., "Functionally Graded Electrospun Polycaprolactone and β-Tricalcium Phosphate Nanocomposites for Tissue Engineering Applications," *Biomaterials* 29:4065-4073 (2008).

Fujihara, K., et al., "Guided Bone Regeneration Membrane Made of Polycaprolactone/Calcium Carbonate Composite Nano-Fibers," *Biomaterials* 26:4139-4147 (2005).

Gauthier, O., et al., "Kinetic Study of Bone Ingrowth and Ceramic Resorption Associated With the Implantation of Different Injectable Calcium-Phosphate Bone Substitutes," *J Biomed Mater Res* 47:28-35 (1999).

Glenn, G.M., et al., "Controlled Release of 2-Heptanone Using Starch Gel and Polycaprolactone Matrices and Polymeric Films," *Polym. Adv. Technol.* 18:636-642 (2007).

Gombotz, W.R., et al., "Stimulation of Bone Healing by TransformingGrowth Factor-Beta 1 Released from Polymeric or Ceramic Implants," *J. Applied Biomaterials* 5:141-150 (1994).

Harrison, B.S., and Atala, A., "Carbon Nanotube Applications for Tissue Engineering," *Biomaterials* 28:344-353 (2007).

Heilmann, F., et al., "Development of Graded Hydroxyapatite/$CaCO_3$ Composite Structures for Bone Ingrowth," *J Mater Sci: Mater Med* 18:1817-1824 (2007).

Hosseinkhani, H., et al., "Bone Regeneration Through Controlled Release of Bone Morphogenetic Protein-2 from 3-D Tissue Engineered Nano-Scaffold," *Journal of Controlled Release* 117:380-386 (2007).

Huang, Y.X., et al., "Preparation and Properties of Poly(lactide-co-glycolide) (PGLA)/Nano-Hydroxyapatite (NHA) Scaffolds by Thermally Induced Phase Separation and Rabbit MSCs Culture on Scaffolds," *J Biomater Appl* 22:409-432 (Mar. 2008).

Jell, G., et al., "Carbon Nanotube-Enhanced Polyurethane Scaffolds Fabricated by Thermally Induced Phase Separation," *J Mater Chem* 18:1865-1872 (2008).

Jones, J.R., et al., "Quantifying the 3D Macrostructure of Tissue Scaffolds," *J Mater Sci: Mater Med* 20:463-471 (2009).

Karande, T.S., et al., "Diffusion in Musculoskeletal Tissue Engineering Scaffolds: Design Issues Related to Porosity, Permeability, Architecture, and Nutrient Mixing," *Annals of Biomedical Engineering* 32(12):1728-1743 (2004).

Khan, Y, et al., "Tissue Engineering of Bone: Material and Matrix Considerations," *J Bone Joint Surg Am* 90(suppl 1):36-42 (2008).

Kofron, M.D., et al., "Novel Tubular Composite Matrix for Bone Repair," *J Biomed Mater Res* 82A:415-425 (2007).

Kong, L., et al., "Preparation and Characterization of a Multilayer Biomimetic Scaffold for bone Tissue Engineering," *J Biomater Appl* 00:1-17 (2007).

Kumar, P.R.A., et al., "Alternate Method for Grafting Thermoresponsive Polymer for Transferring in Vitro Cell Sheet Structures," *J Appl Polym Sci* 105:2245-2251 (2007).

Kumar, P.R.A., et al., "Rapid and Complete Cellularization of Hydroxyapatite for Bone Tissue Engineering," *Acta Biomaterialia* 1:545-552 (2005).

Laffargue, PH., et al., "Evaulation of Human Recombinant Bone Morphogenetic Protein-2-Loaded Tricalcium Phosphate Implants in Rabbits' Bone Defects," *Bone* 25(suppl 2):55S-58S (1999).

Laurencin, C.T., et al., "A Highly Porous 3-Dimentional Polyphosphazene Polymer Matrix for Skeletal Tissue Regeneration," *J Biomedical Materials Research* 30:133-138 (1996).

Lyckfeldt, O. and Ferreira, J.M.F., "Processing of Porous Ceramics by 'Starch Consolidation'", *J European Ceramic Society* 18:131-140 (1998).

MacDonald, R.A., et al., "Collagen-Carbon Nanotube Composite Materials as Scaffolds in Tissue Engineering," *J Biomed Mater Res* 74A:489-496 (2005).

Matsuda, N., et al., "Tissue Engineering Based on Cell Sheet Technology," *Adv. Mater.* 19:3089-3099 (2007).

McIntosh, L., et al., "Impact of Bone Geometry on Effective Properties of Bone Scaffolds," *Acta Biomaterialia* 5:680-692 (2009).

Murugan, R., et al., "Nanofibrous Scaffold Engineering Using Electrgospinning," *J. Nanosci Nanotechnol* 7:4595-603 (2007).

Pham, Q.P., et al., "Electrospun Poly(ϵ-caprolactone) Microfiber and Multilayer Nanofiber/Microfiber Scaffolds: Characterization of Scaffolds and Measurement of Cellular Infiltration," *Biomacromolecules* 7:2796-2805 (2006).

Price, R.L., et al., "Selective Bone Cell Adhesion on Formulations Containing Carbon Nanofibers," *Biomaterials* 24:1877-1887 (2003).

Quinn, J.F. and Caruso, F., "Stabilization of Hydrogen-Bonded Poly(N-isopropylacrylamide) Multilayers by a Dual Electrostatic/Hydrogen Bonding Copolymer," *Aust. J. Chem.* 58:442-446 (2005).

Ren, Li-L., et al., "A Novel Strategy for Prefabrication of Large and Axially Vascularized Tissue Engineered Bone by Using an Arteriovenous Loop," *Medical Hypotheses* 71:737-740 (2008).

Rezwan, K., et al., "Biodegradable and Bioactive Porous Polymer/Inorganic Composite Scaffolds for Bone Tissue Engineering," *Biomaterials* 27:3413-3431 (2006).

Ritger, P.L. and Peppas, N.A., "A Simple Equation for Description of Solute Release I. Fickian and Non-Fickian Release From Non-Swellable Devices in the Form of Slabs, Spheres, Cylinders or Discs," *J. of Controlled Release* 5:23-36 (1987).

Salvetat, J.-P., et al., "Mechanical Properties of Carbon Nanotubes," *Appl Phys A* 69:255-260 (1999).

Schmidmaier, G., et al., "Biodegradable Poly(D,L-Lactide) Coating of Implants for Continuous Release of Growth Factors," *J Biomed Mater Res* 58:449-455 (2001).

Shi, X., et al., "Fabrication of Porpus Ultra-Short Single-Alled Carbon Nanotube Nanocomposite Scaffolds for Bone Tissue Engineering," *Biomaterials* 28:4078-4090 (2007).

Shi, X., et al., Injectable Nanocomposites of Single-Walled Carbon Nanotubes and Biodegradable Polymers for Bone Tissue Engineering, *Biomacromolecules* 7:2237-2242 (2006).

Silva, M.M.C.G., et al., "The Effect of Anisotropic Architecture on Cell and Tissue Infiltration Into Tissue Engineering Scaffolds," *Biomaterials* 27:5909-5917 (2006).

Sitharaman, B., et al., "In Vivo Biocompatibility of Ultra-Short Single-Walled Carbon Nanotube/Biodegradable Polymer Nanocomposites for Bone Tissue Engineering," *Bone* 43:362-370 (2008).

Smith, L.A. and Ma., P.X., "Nano-Fibrous Scaffolds for Tissue Engineering," *Colloids and Surfaces B: Biointerfaces* 39:125-131 (2004).

Soriano, I. and Evora, C., "Formulation of Calcium Phosphates/poly (d,l-lactide) Blends Containing Gentamicin for Bone Implantation," *J Controlled Release* 68:121-134 (2000).

Stevens, M.M., "Biomaterials for bone tissue engineering," *Materialstoday* 11(5):18-25 (2008).

Sun, Jui-S., et al., "The Effects of Calcium Phosphate Particles on the Growth of Osteoblasts," *J Biomed Mater Res* 37:324-334 (1997).

Supronowicz, P.R., et al., "Novel Current-Conducting Composite Substrates for Exposing Osteoblasts to Alternating Current Stimulation," *J Biomed Mater Res* 59:499-506 (2002).

Tang, Z., et al., "Biomedical Applications of Layer-by-Layer Assembly: From Biomimetrics to Tissue Engineering," *Adv Mater* 18:3203-3224 (2006).

Teng, S-H., et al., "Collagen/Hydorxyapatite Composite Nanofibers by Electrospinning," *Materials Letters* 62:3055-3058 (2008).

Thoma, K., et al., "Biodegradable Controlled Release Implants Based on β-Tricalcium Phosphate Ceramic," *Eur. J. Pharm., Biopharm.* 38(3):107-112 (1992).

Tsuruga, E., et al., "Pore Size of Porous Hydroxyapatite as the Cell-Substratum Controls BMP-Induced Osteogenesis," *J. Biochem.* 121:317-324 (1997).

Valentini, L., et al., "Frequency Dependent Electrical Transport Between Conjugated Polymer and Single-Walled Carbon Nanotubes," *Diamond and Related Materials* 12:1601-1609 (2003).

Valmikinathan, C.M., et al., "Novel Nanofibrous Sprial Scaffolds for Neural Tissue Engineering," *J. Neural Eng*, 5:422-432 (2008).

Venugopal, J., et al., "Mineralization of Osteoblasts With Electrospun Collagen/Hydroxyapatite Nanofibers," *J Mater Sci: Mater Med* 19:2039-2046 (2008).

Verdejo, R., et al., "Reactive Polyurethane Carbon Nanotube Foams and Their Interactions With Osteoblasts," *J Biomed Mater Res* 88A:65-73 (2009).

Wang, J., et al., "Enhanced Osteoblast Response to 3D Sprial Nanofibrous Scaffolds in Rotating Wall Vessel (RWV) Bioractors," Annual Conference of Orthopedics Research Society (ORS), Las Vegas, NV, Feb. 2009.

Wang, J., et al., "Spiral-Structured, Nanofibrous, 3D Scaffolds for Bone Issue Engineering," *J Biomed Mater Res* 00A:1-11 (2009).

Wang, J., et al., "The Effect of Fiber Layer Thickness on the Bioactivity of Nanofibrous 3D Scaffolds for Bone Tissue Engineering," Annual Conference & Exposition of TERMIS, San Diego, CA, Dec. 2008.

Wang, J., et al., "The Influence of Fiber Thickness, Wall Thickness and Gap Distance on the Sprial Nanofibrous Scaffolds for Bone Tissue Engineering," *Mater. Sci. Eng.* C:1-7 (2009).

Wang, S.-F., et al., "Preparation and Mechanical Properties of Chitosan/Carbon Nanotubes Composites," *Biomacromolecules* 6:3067-3072 (2005).

Woo, K.M., et al., "Nano-Bibrous Scaffolding Promotes Osteoblast Differentiation and Biomineralization," *Biomaterials* 28:335-343 (2007).

Xu, S., et al., "RF Plasma Sputtering Deposition of Hydroxyapatite Bioceramics: Synthesis, Performance, and Biocompatibility," *Plasma Process. Polym.* 2:373-390 (2005).

Yang, J., et al., "Cell Delivery in Regenerative Medicine: the Cell Sheet Engineering Approach," *Journal of Controlled Release* 116:193-203 (2006).

Yang, J., et al., "Reconstruction of Functional Tissues With Cell Sheet Engineering," *Biomaterials* 28:5033-5043 (2007).

Yasuda, H.Y., et al., "Preparation of Hydroxyapatite/α-Tricalcium Phosphate Composites by Colloidal Process," *Science and Technology of Advanced Materials* 3:29-33 (2002).

Yu, H., et al., "Improved Tissue-Engineered Bone Regeneration by Endothelial Cell Mediated Vascularization," *Biomaterials* 30:508-517 (2009).

Zanello, L.P., et al., "Bone Cell Proliferation on Carbon Nanotubes," *Nano Letters* 6(3): 562-567 (2006).

Zhang, L. and Webster, T.J., "Nanotechnology and nanomaterials: Promises for improved tissue regeneration," *Nano Today* 4:66-80 (2009).

Zhang, X., et al., "Poly(vinyl alcohol/SWNT Composite Film," *Nano Letters* 3(9):1285-1288 (2003).

Notification of Transmittal of the International Search Report (ISR) and the Written Opinion (WO) of the International Searching Authority, or the Declaration, with copies of the ISR and WO, PCT/US2010/037256, mailed Jul. 21, 2010.

Office Action, U.S. Appl. No. 12/586,345, dated Mar. 9, 2011[*].

Liveny, Y., "Milk proteins as vehicles for bioactives", *Current Opinion in Colloid & Interface Science*, vol. 15; pp: 73-83 (2009).

Notification of Transmittal of the International Search Report and the Written Opinion of the International Searching Authority, or the Declaration, PCT/US2011/035881, mailed Jan. 17, 2012.

Notification Concerning Transmittal of International Preliminary Report on Patentability (IPRP) with IPRP, PCT/US2011/035881, mailed Nov. 22, 2012.

AU 2011251991, 1st Office Action, dated Apr. 18, 2013.

[*] cited by examiner

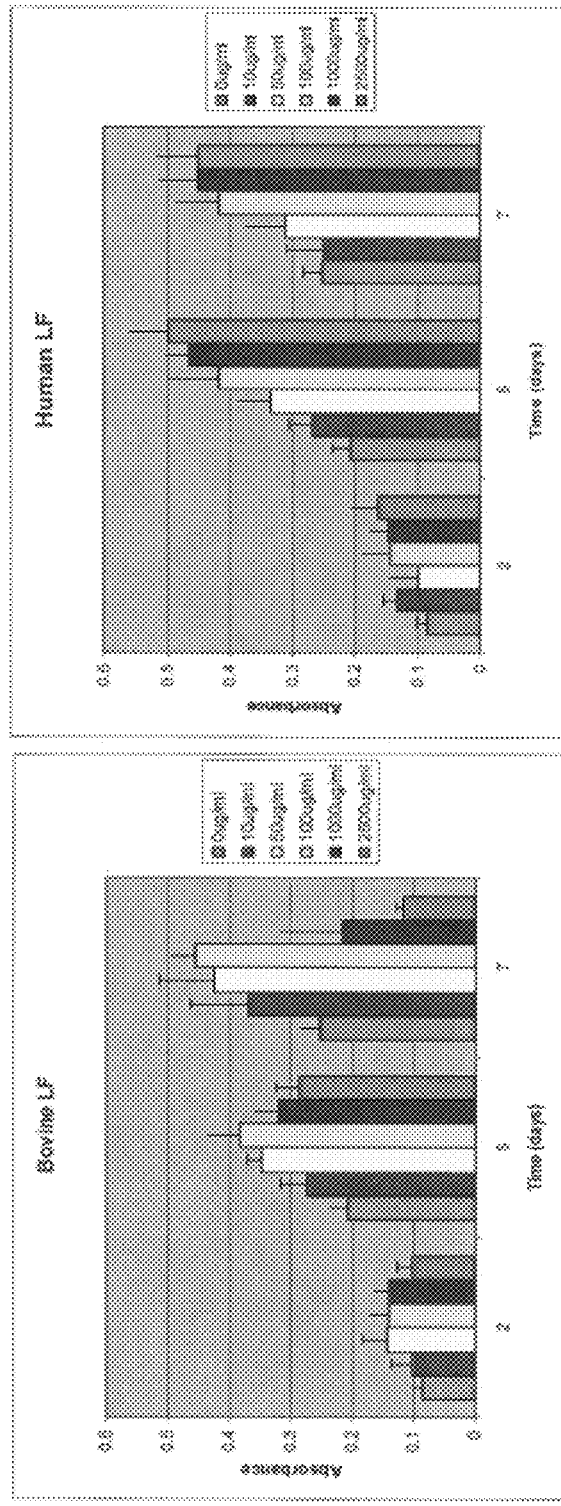
FIGS. 1A and 1B. Viability of passage -3 human mesenchymal stem cells as a function of time. A. Cells fed with media containing different concentrations of bovine LF. B. Cells fed with media containing different concentrations of human LF.

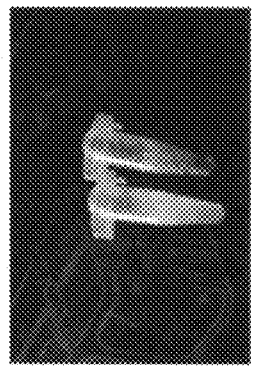
FIG. 2A
Aqueous solutions of tyrosinated lactoferrin: low and high concentrations.
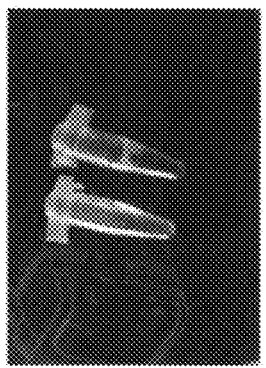
FIG. 2B
Tyrosinated lactoferrin gel after enzymatic cross-linking-low and high concentrations
FIGS. 2A and 2B
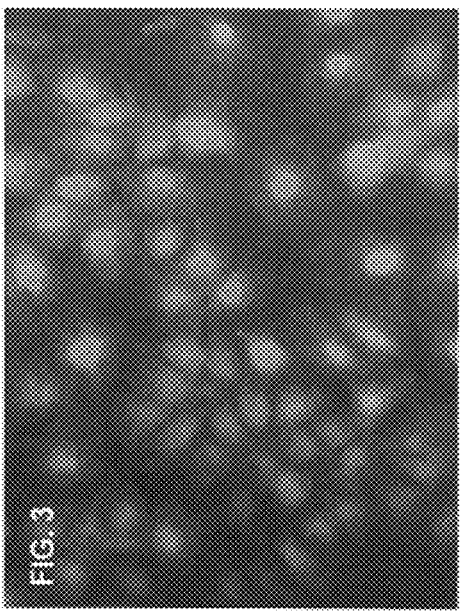
FIG. 3

FIG. 4A Gels prepared from 100ug solution (green color shows live cells)

FIG. 4B Gels prepared from 100ug solution (green color shows live cells) – high mag 10X –showing well spread cells FIG. 4C Gels prepared from 100ug solution (green color shows live cells) – high mag 10X –showing well spread cells FIG. 4D Photomicrograph of cell seeded Gels prepared from 100ug solution

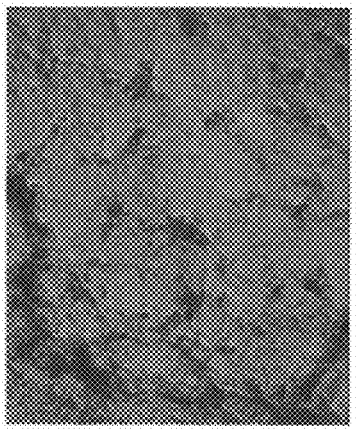
FIG. 5B Photomicrograph of cell seeded gels prepared from 200ug solution
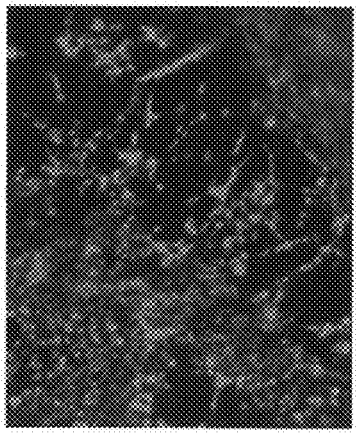
FIG. 6B Photomicrograph cell seeded Gels prepared from 1000ug solution darker image due to higher concentration of the protein in the gel
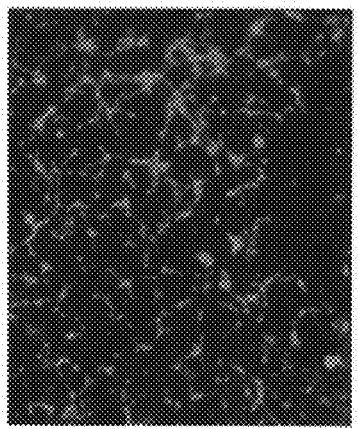
FIG. 5A Gels prepared from 200 solution (green color shows live cells)
FIG. 6A Gels prepared from 1000ug solution (green color shows live cells)
FIGS. 5A and 5B
FIGS. 6A and 6B

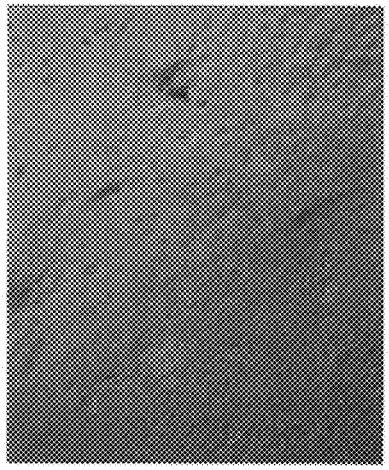
FIG. 7A
100ug/ml lactoferrin added to the media
FIG. 7B
200ug/ml lactoferrin added to the media
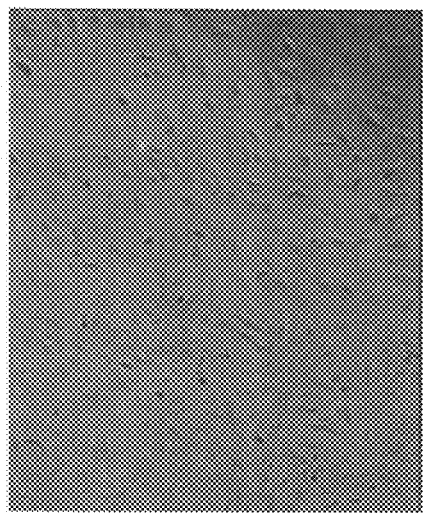
FIG. 7C
1000ug/ml lactoferrin added to the media
FIGS. 7A-7C Cells encapsulated in lactoferrin biomatrix and cultured for 7 days. Cells are viable inside the gel and some cells started migrating out of the gel after 7 days

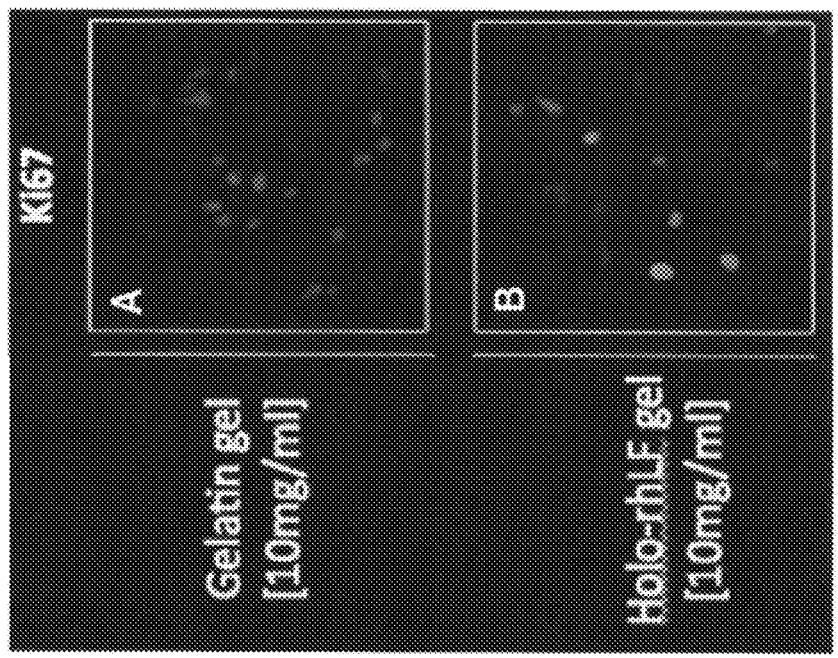
FIGS. 24A-B
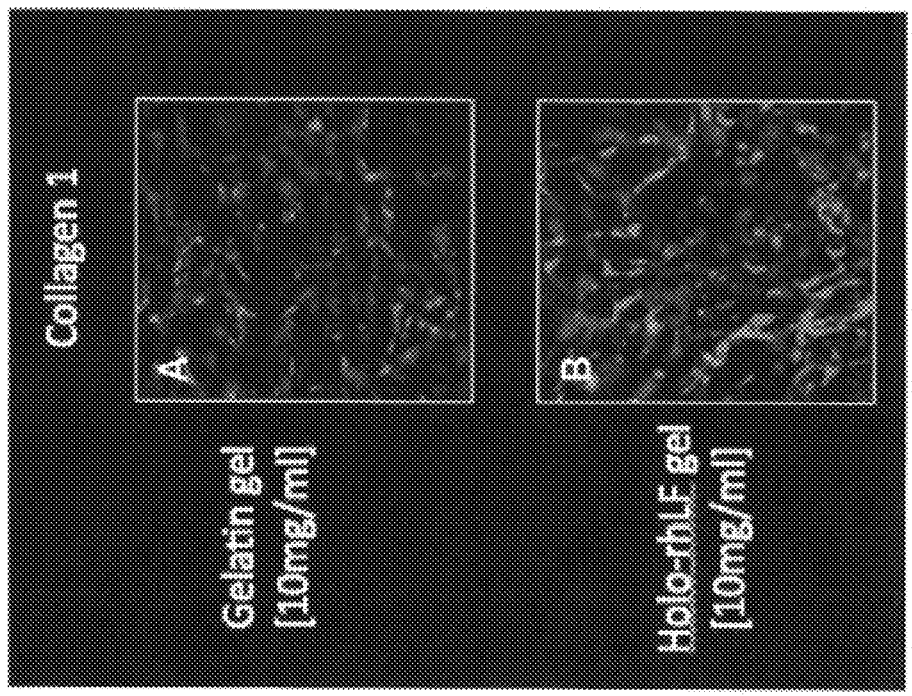
FIGS. 23A-B

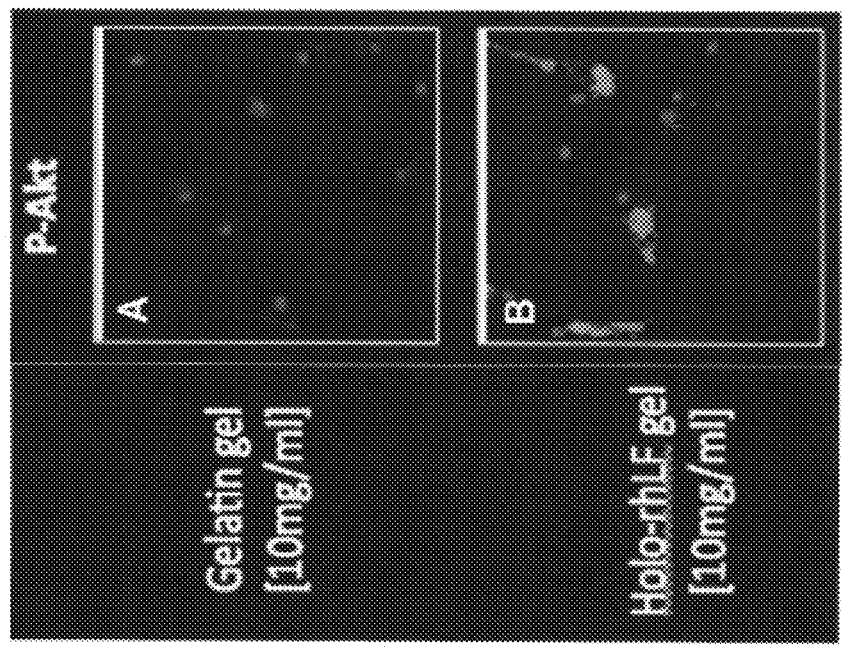
FIGS. 26A-B
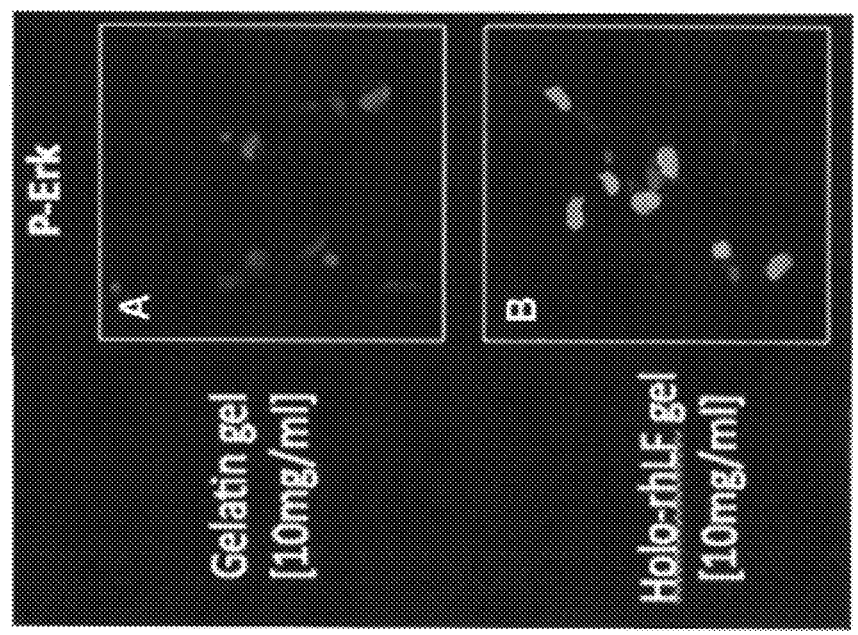
FIGS. 25A-B

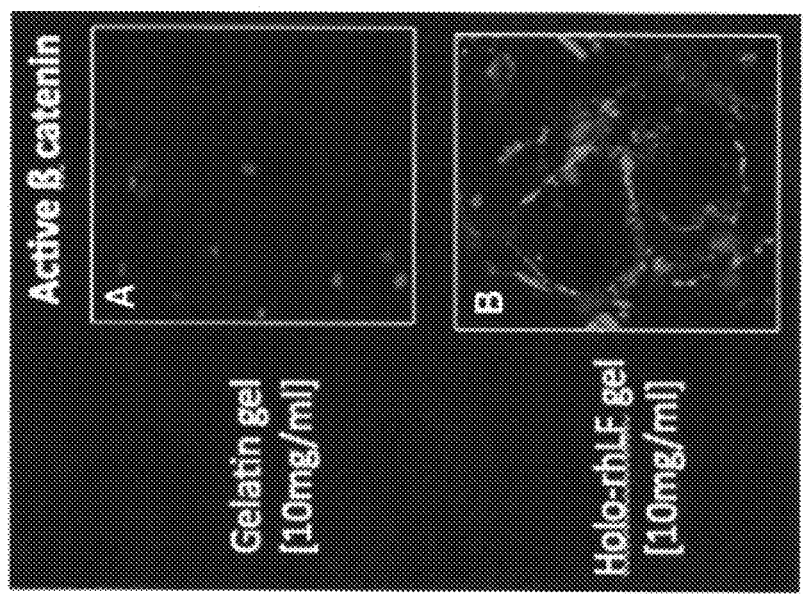
FIGS. 27A-B

LACTOFERRIN-BASED BIOMATERIALS FOR TISSUE REGENERATION AND DRUG DELIVERY

RELATED APPLICATION

This application claims the benefit of U.S. Provisional Application No. 61/332,935, filed on May 10, 2010.

The entire teachings of the above application are incorporated herein by reference.

BACKGROUND OF THE INVENTION

There is a significant clinical need for hard and soft tissue grafting for the reconstruction of musculoskeletal damage due to trauma, chronic disease and congenital anomalies. Bone and/or cartilage grafts are often used to assist in the repair or healing of musculoskeletal damage. Such grafts of natural tissues, such as cortical or cancellous bone, can be autografts, allografts or xenografts. Autografts are "self" grafts of bone and/or cartilage taken from a donor site in the patient and transplanted to the host site of the same patient. Allografts are grafts transplanted from a donor of the same species as the intended recipient, but are not autografts, i.e., the graft comes from another patient or a cadaver. Xenografts are grafts taken from a different species from the intended recipient.

Autografts harvested from the patient at the time of surgery are the standard for grafting. Autografts have been shown to promote bone growth at the site of grafting (osteoinductive), form new bone themselves (osteogenic) and provide a scaffold for bone ingrowth (osteoconductive). Advantageously, as autografts are harvested from the same patient in which they are to be transplanted, there is little or no risk of "rejection" of the graft or of transmitting viruses. Unfortunately, a patient has a limited supply of donor bone for grafting. Additionally, autografts can often suffer from donor site morbidity.

Allografts and xenografts are available in greater supply than autografts. However, they are less osteoinductive, they may induce a greater immunogenic response (e.g., inflammation, graft rejection, etc.) and they suffer from a higher risk of disease transfer compared to autografts. As a result, adjunct therapies are often used with allografts and xenografts to augment and/promote bone regeneration and repair.

Adjunct therapies include the use of biomaterials that promote cellular infiltration and osteogenesis and biologics such as bone morphogenetic proteins (BMPs), which stimulate cell replication and activity. While these adjuvant therapies increase graft remodeling and new bone formation, they are costly and include risk factors such as osteosarcoma, marrow fibrosis and ectopic bone formation. The use of allografts and xenografts to augment bone healing is expensive and the failure rate is relatively high.

Alternative, musculoskeletal graft substitutes continue to be researched. The ideal material for musculoskeletal regeneration is a biomaterial that is biocompatible, capable of supporting biological integration and full restoration of native tissue, and is preferably biodegradable. Furthermore, it is preferred that bone graft substitutes favorably interact with a variety of host cells involved in tissue regeneration and integration. However, despite the extensive research in this field, synthetic bone graft substitutes often fail to meet all of these criteria. Thus, there is a need to provide a biocompatible material that can be used as a musculoskeletal graft substitute having the properties suitable for musculoskeletal repair and regeneration, and methods for making such materials.

SUMMARY OF THE INVENTION

The clinical needs of tissue grafting for the reconstruction of trauma, chronic diseases and congenital anomalies are substantial. The ideal material for musculoskeletal regeneration is a biomaterial that fosters biological integration and full restoration of native tissue, and which interacts favorably with a variety of host cells involved in tissue regeneration and integration.

The regenerative biomaterial described herein is an innovative and transformative approach to musculoskeletal tissue regeneration, through the use of a multifunctional, biodegradable matrix designed to favorably modulate the functions of different cell types involved in musculoskeletal tissue regeneration. Thus, one aspect of the invention is a biomatrix composition comprising, consisting essentially of, or consisting of, cross-linked lactoferrin ("LF"). In one embodiment, the cross-linked lactoferrin is developed or produced using tyrosinated lactoferrin. In another embodiment, the cross-linked lactoferrin is a radio-opaque cross-linked lactoferrin. In a further embodiment, the biomatrix composition is an injectable composition. An injectable composition of the present invention can be a gel.

In a further embodiment, the biomatrix composition further comprises a solid matrix. In one embodiment, the solid matrix comprises, consists essentially of, or consists of: nano and/or micro metallic components such as biocompatible/bioactive metals such as silver, gold, iron, calcium, magnesium, and combinations thereof; polymeric components (for example, nano spheres, micro spheres, particles and combinations thereof) of biodegradable polymers such as polyesters, polyurethanes, polyanhydrides, peptides, proteins and polysaccharides; ceramic particles (such as calcium phosphate, hydroxyapatite, bioactive glass, and combinations thereof), in various forms, such as for example and without limitation, spheres, tubes, fibers and wires. In one embodiment, the solid matrix comprises, consists essentially of, or consists of calcium phosphate.

In another embodiment, the biomatrix composition comprises at least 100 ug/ml, or at least 100 ug/cm$^3$, to at least 50,000 ug/ml, or at least 50,000 ug/cm$^3$ of cross-linked lactoferrin.

In a further embodiment, the biomatrix can be a composite with other natural and synthetic polymers. In another embodiment, the biomatrix can be (bio)degradable using hydrolytically or enzymatically degradable components in the matrix. Thus, in one embodiment, a biodegradable biomatrix as described herein is hydrolytically degradable, enzymatically degradable, or a combination thereof.

Typical diseases or clinical conditions involving bone defects that would benefit from musculoskeletal regeneration using the biomatrix compositions described herein include conditions such as osteoporosis, osteopenia, osteomyelitis, osteonecrosis (also called avascular necrosis, aseptic necrosis, or ischemic bone necrosis) and Paget's disease. Trauma-induced bone defects (e.g., breakage, fractures) and other disease conditions, for example, bone tumors (e.g., osteosarcoma), or congenital deformities would also benefit from reconstruction or grafting using the biomatrix compositions described herein.

Also provided herein are methods of preparing and producing a biomatrix composition as described herein, and the biomatrix compositions prepared or produced thereby.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B are graphs demonstrating the viability of passage-3 human mesenchymal stem cells as a function of time in the presence or absence of varying concentrations of LF. FIG. 1A graph cells treated with media containing increasing concentrations of bovine LF. FIG. 1B graphs cells treated with media containing increasing concentrations of human LF.

FIGS. 2A and 2B are photographs of biomatrix materials described herein. FIG. 2A is a photograph of two eppendorf tubes containing aqueous solutions of tyrosinated lactoferrin: low (left) and high (right) lactoferrin concentrations. In this example, 1000 ug/ml was the low concentration of tyrosinated lactoferrin, and 30,000 ug/ml was the high concentration of tyrosinated lactoferrin. FIG. 2B is a photograph of two eppendorf tubes containing the tyrosinated lactoferrin gel after enzymatic crosslinking of low (left) and high (right) concentrations of lactoferrin.

FIG. 3 demonstrates the viability of human mesenchymal stem cells on tyrosinated lactoferrin film. FIG. 3 is a photograph demonstrating the viability of human mesenchymal stem cell on tyrosinated lactoferrin film.

FIGS. 4A-C: The cells were stained with live/dead fluorescent staining to demonstrate the presence of well spread viable cells in/on the matrix. FIG. 4D: The optical photomicrographs of the samples are included for comparison.

FIGS. 5A and 5B are photographs of cells seeded on lactoferrin based gels (200 ug). The lactoferrin-based gel was prepared as described herein. Briefly, 200 ug of tyrosinated lactoferrin (200 ug), horse radish peroxidase (HRP) and H$_2$O$_2$ were added to a tissue culture well and allowed to gel. Cells were seeded on top of the gel and 1 mL of fresh media without lactoferrin was added. MC3T3-E1 preostoeblastic cells were seeded on lactoferrin based gels as soon as it was prepared (to prevent gel drying; right). FIG. 5A: The cells were stained with live/dead fluorescent staining to demonstrate the presence of well spread viable cells in/on the matrix. FIG: 5B: The optical photomicrographs of the samples are included for comparison.

FIGS. 6A and 6B are photographs of cells seeded on lactoferrin based gels (1,000 ug). As described herein, the lactoferrin based gel was made with 1000 ug of tyrosinated lactoferrin and after gelation 1 mL of the media was added to cells seeded on the gel. MC3T3-E1 preostoeblastic cells were seeded on lactoferrin based gels as soon as it was prepared (to prevent gel drying). FIG. 6A: The cells were stained with live/dead fluorescent staining to demonstrate the presence of well spread viable cells in/on the matrix. FIG. 6B: The optical photomicrographs of the samples are included for comparison.

FIGS. 7A-7C are optical photomicrographs of MC3T3 cells cultured on tissue culture polystyrene dishes in the presence of 100 ug/ml, 200 ug/ml and 1000 ug/ml of lactoferrin added to the media.

As seen in FIG. 8, cells remained alive and healthy, confirming the cytocompatability of the biomatrix gel and the gelation process. Healthy cells are seen both encapsulated and outside the biomatrix gel at day 7.

FIG. 9A is a confocal image MC3T3-E1 cells cultured on the surface of a tissue culture plate (TCP). FIG. 9B is a confocal image MC3T3-E1 cells cultured in bovine lactoferrin gel. MC3T3-E1 cells cultured in the lactoferrin gel grow in 3D with long prosthesis (see FIG. 9B).

FIG. 19A is a confocal image of human mesenchymal stem cells cultured on the surface of tissue culture plate (TCP). FIG. 10B is a confocal image of human mesenchymal stem cells cultured in bovine lactoferrin gel for 3 days Human mesenchymal stem cells showed growth in three dimension when cultured in the gel.

FIG. 13A shows the results of holo- rhLf at different concentrations in 100 µl of 10 U HRP+0.75 µl of 0.25% H$_2$O$_2$. FIG. 13B shows the results apo-rhLf at different concentrations in 100 µl of 10 U HRP+ 0.75 µl of 0.25% H$_2$O$_2$.

FIGS. 23A-23B are photographs demonstrating deposition of collagen I matrix by cells encapsulated in lactoferrin gel (FIG. 23B) and gelatin gel (FIG. 23A). The cell nucleus was stained in red and collagen was stained in green. Cells encapsulated in lactoferrin showed a significant increase in collagen matrix deposition compared to cells encapsulated in gelatin.

FIGS. 24A-24B are photographs demonstrating that cells encapsulated in lactoferrin gel retain the ability to undergo cell proliferation. A significant number of multiplying cells after 48 h in lactoferrin gel is seen in FIG. 24B as compared to the number of multiplying cells after 48 h in gelatin gel (FIG. 24A). Cell nuclei are stained red with propidium iodide nuclear stain; multiplying cells are stained green with Ki67 and FITC-conjugated secondary antibodies.

FIGS. 25A-25B are photographs demonstrating that cells encapsulated in lactoferrin gel (FIG. 25B) induces significant phosphorylation of ERK compared to cells encapsulated in gelatin gel (FIG. 25A). Cell nuclei are stained red with propidium iodide nuclear stain; green fluorescence indicates the presence of phosphorylated ERK, which plays a very important role on cell proliferation and osteogenic differentiation.

FIGS. 26A-26B are photographs demonstrating that cells encapsulated in lactoferrin gel (FIG. 26B) induces significant phosphorylation of AKT as compared to cells encapsulated in gelatin gel (FIG. 26A). Cell nuclei are stained red with propidium iodide nuclear stain; green fluorescence indicates the presence of phosphorylated AKT. indicating activation of the anti-apoptotic pathway.

FIGS. 27A-27B are photographs demonstrating that cells encapsulated in lactoferrin gel (FIG. 27B) show a significant presence of active beta-catenin in cells encapsulated indicating the osteogenic activity of the cells in lactoferrin gel as compared to cells in gelatin gel (FIG. 27A). Cell nuclei are stained red with propidium iodide nuclear stain; green fluorescence indicates the presence of active beta-catenin.

DETAILED DESCRIPTION OF THE INVENTION

Figure 4A:
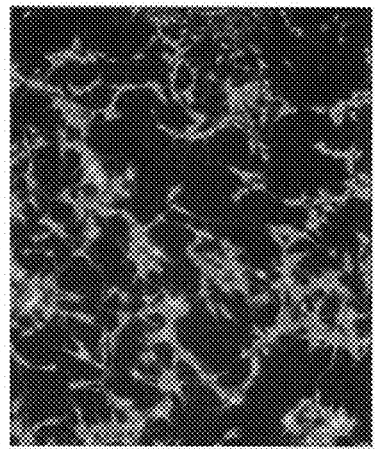
FIGS. 4A-4D are photographs of cells in 48 well plates (0.75 cm$^2$) seeded on lactoferrin based gels made from 100 µg of tyrosinated lactoferrin per well. The cells were cultured on the lactoferrin gel in 1 mL of media (without lactoferrin) as described herein. MC3T3-E1 preostoeblastic cells were seeded on lactoferrin based gels as soon as it was prepared (to prevent gel drying).
Figure 4B:
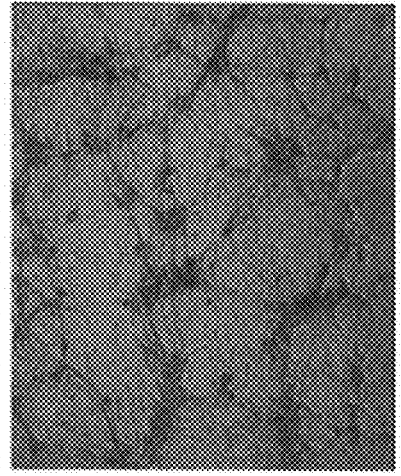
Figure 4C:
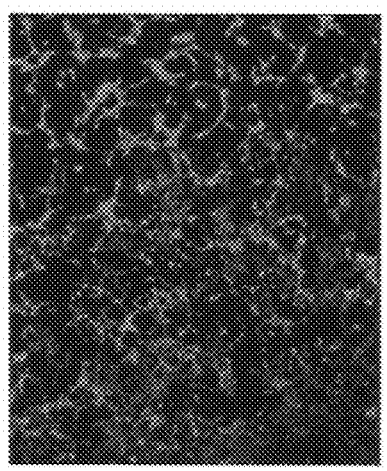
Figure 4D:
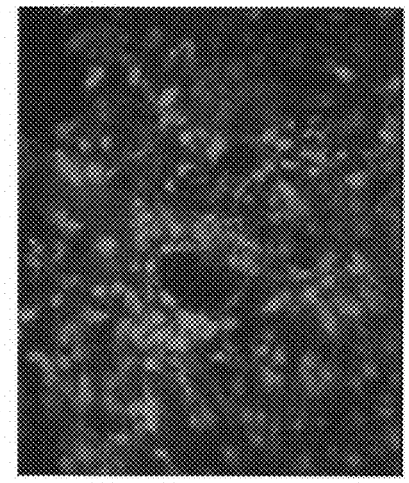

The term "tissue engineering" was coined in 1987 during a National Science Foundation (NSF) meeting inspired by a concept presented by Dr. Y. C Fung [Heineken F G, Skalak R. Tissue Engineering: A brief overview. J Biomech Eng 113, 111 (1991)]. The field of tissue engineering has now developed into a highly interdisciplinary science and has attempted to recreate or regenerate almost every type of human tissue and organ [Fuchs J R, Nasseri B A, Vacanti J P. Tissue Engineering: A $21^{st}$ century solution to surgical reconstruction. Ann Thorac Surg 72, 577 (2001)]. One of the ultimate goals of tissue engineering is to address the need for materials in bone and cartilage grafting, in other words, develop an alternative therapeutic strategy to autografting and allografting. Autografting harvests tissue from the patient at the time of surgery and are the standard for bone grafting.

Several approaches are currently used to repair or recreate damaged tissue using the principles of tissue engineering. Among these, scaffold-based tissue engineering, where biomaterials are used alone or in combination with cells and/or biologically active molecules, is one of the most attractive and extensively investigated approaches. The function of the biomaterials and scaffolds is to guide the regenerating tissue and provide appropriate structural support. As such, biomaterials and scaffolds mimic the structure and functions of natural extracellular matrix (ECM).

The interest in biomaterials for tissue engineering led to the significant development in biodegradable, non-cytotoxic materials that can be fabricated into structures that closely resemble the ECM [Nair L S and Laurencin C T (Eds). Nanotechnology and Tissue Engineering: The Scaffold. CRC Press, Taylor and Francis (June, 2008)]. Studies during the past 10-15 years have demonstrated the feasibility of programming these materials to exhibit desired properties such as mechanical strength, ECM like morphology and structure and bioactive ligand presentation by controlled drug delivery mechanism or decorating the structures with bioactive peptides [Kaplan D L, Moon R T, Vunjak-Novakovic G. It takes a village to grow a tissue. Nat Biotechnol. 23, 1237 (2005); Matsumoto T, Mooney D J. Cell instructive polymers. Adv Biochem Eng Biotechnol. 102, 113 (2006); Lutolf M P, Hubbell J A. Synthetic biomaterials as instructive extracellular microenvironments for morphogenesis in tissue engineering. Nat Biotechnol 23, 47 (2005); Hollister S J. Porous scaffold design for tissue engineering. Nat Mater 4, 518 (2005)]. Also, research to date has identified different cell sources including stem cells which, when combined with degradable matrices can form three dimensional living structures. These techniques have led to the development of many tissues in the laboratory scale such as bone, ligament, tendon, heart valves, blood vessels, myocardium, esophagus and trachea. However, several engineering and biological challenges still remain for successful clinical translation of the laboratory research to make tissue engineering a reliable route for organ/tissue regeneration. One of the most important challenges is to ensure proper in vivo performance of the engineered cell-scaffold constructs under challenging microenvironmental conditions of inflammation characteristic of damaged tissues [Lumelsky N L. Commently: Engineering of Tissue Healing and Regeneration. Tissue Engineering. 13, 1: (2007)]. This necessitates the development of cell instructive biomaterial structures that can communicate with host cells via multiple regulatory signals.

Recent advances in biomaterial science and bioengineering has presented a variety of options to develop scaffolds for regenerative medicine. The studies so far has indicated that scaffold based regeneration depends on several factors including scaffold chemistry, rate of degradation, physical and biological properties. Further studies have focused on adsorbing or encapsulating various biological factors that regulate cellular functions in various scaffolds [Chu T.-M. G., Warden S. J., Turner C. H., Stewart R. L. Segmental bone regeneration using a load-bearing biodegradable carrier of bone morphogenetic protein-2. Biomaterials 28:459 (2007); Gomez G., Korkiakoski S., Gonzalez M. M., Lansman S., Ella V., Salo T., Kellomaki M., Ashammakhi N., Arnaud E. Effect of FGF and polylactide scaffolds on calvarial bone healing with growth factor on biodegradable polymer scaffolds. J. Craniofac. Surg. 17:935 (2006)]. However, the major limitation observed in most of these studies is the significant and dramatic decrease in the concentration of the adsorbed/encapsulated factors soon after implantation due to rapid and uncontrolled diffusion.

New directions were explored to address this limitation by developing scaffolds with tethered growth factors. One such study involves developing scaffolds with metal metalloproteinase (MMP) recognition sites, which facilitated the release of the encapsulated BMP-2 over a prolonged time [Lutolf M. P., Weber F. E., Schmoekel H. G., Schense J. C., Kohler T., Muller R., Hubbell J. A. Repair of bone defects using synthetic mimetics of collagenous extracellular matrices. Nat. Biotechnol. 21:513 (2003)]. Another strategy to regulate scaffold-mediated growth factor delivery involved tethering the bioactive factor BMP-2 to a polymeric scaffold using a biodegradable PEG link. This was shown to help maintain the local influence for a prolonged time and demonstrated significantly greater bone formation in the BMP-2 tethered group relative to control groups [Liu H. W., Chen C. H., Tsai C. L., Lin I. H., Hsiue G. H. Heterobifunctional poly(ethylene glycol)-tethered bone morphogenetic protein-2-stimulated bone marrow mesenchymal stromal cell differentiation and osteogenesis. Tissue Eng. 13:1113 (2007)].

Recent studies showed the feasibility to attain still higher efficacy by covalently immobilizing these factors on scaffolds. However, covalent immobilization of biologically active molecules raises concerns such as whether the chemical immobilization process affect the bioactivity, and whether internalization of the growth factors is required for eliciting appropriate biological responses.

Described herein is a novel regenerative biomaterial and methods of use thereof which significantly advance the current materials and their use as synthetic scaffolds in musculoskeletal regeneration. As used herein, a "regenerative biomaterial" (also referred to herein as a "biomatrix" or a "biomatrix composition") refers to a material that favorably modulates the response(s) of a variety of cell types involved in wound healing to support tissue regeneration. In addition to influencing tissue specific cells (e.g., osteoclasts, osteoblasts), a regenerative biomaterial preferably exerts control of the inflammatory tissue microenvironment (e.g., affecting inflammatory responses of cells, affecting potency of inflammatory mediators such as inflammatory cytokines or free radicals), for example, by decreasing or reducing inflammation, which in turn, enhances tissue regeneration. In one embodiment, a regenerative biomaterial as described herein is suitable for musculoskeletal (e.g., bone, cartilage, tendon and/or muscle) tissue regeneration.

In one embodiment, the biomatrix compositions or regenerative biomaterials described herein are used to support the regeneration of tissue that is diseased or compromised due to, or resulting from, a clinical condition such as osteoporosis, osteopenia, osteomyelitis, osteonecrosis (also called avascular necrosis, aseptic necrosis, or ischemic bone necrosis) or Paget's disease. Trauma-induced bone defects (e.g., breakage, fractures) and other disease conditions, for example, bone tumors (e.g., osteosarcoma), or congenital deformities would also benefit from reconstruction or grafting using the biomatrix compositions or regenerative biomaterials described herein.

As described herein, the regenerative biomaterial comprises, consists essentially of, or consists of cross-linked lactoferrin ("LF"). Lactoferrin is an iron-binding protein occurring in various external secretions as well as in the specific granules of neutrophilic leukocytes [Spik G, Legrand D, Mazurier J, Pierce A, Perraudin J (Ed). Advances in Lactoferrin Research in Advances in experimental medicine and biology. 443, Plenum Press, New York (1998)]. Thus, as used herein, cross-linked lactoferrin refers to both cross-linked lactoferrin without iron, and cross-linked lactoferrin with various iron content or saturation. Lactoferrin is present in tears and in nasal, salivary, bronchial, pancreatic, stomach, gastrointestinal and genital secretions. Serum levels of lactoferrin in healthy subjects range from 2-7 µg/ml and are predominantly neutrophil derived, but during inflammation and sepsis its local concentrations can be much higher [Coccavo D, Sebastiani G D, Di Monaco C, Guido F, Galeazzi M, Ferri G M, Bonomo I, Afeltra A. Increased levels of lactoferrin in synovial fluid but not in serum from patients with rheoumatoid arthritis. Int J Clin Lab Res 29: 30 (1999)]. Lactoferrin has attracted increasing scientific interest since the early 1960s due to its high concentration in human breast milk [LoEnnerdal B & Iyer S Lactoferrin: molecular structure and biological function. Annual Review of Nutrition 15, 93 (1995)]. Highest levels of lactoferrin have been detected in the lactating mammary gland, where levels up to 6 g/liter have been detected in colostrums [Masson P L, Heremans J F. Lactoferrin in milk from different species. Comp Biochem Physiol B. 39: 316 (1971)]. Lactoferrin resembles serum transferrin with respect to metal-chelating properties, both proteins being able to bind two atoms of iron. However, the iron-lactoferrin complex is more stable at low pH and also lactoferrin differs from transferrin in amino acid and carbohydrate composition, peptide map patterns and antigenic properties.

Lactoferrins are single chain polypeptides of about 80,000 Da containing 1-4 glycans, depending on the species [Spik G, Coddeville B, Mazurier J, Bourne Y, Cambillaut C & Montreuil J Primary and three-dimensional structure of lactotransferrin (lactoferrin) glycans. Advances in Experimental Medicine and Biology 357, 21 (1994)]. Bovine and human lactoferrins consist of 689 and 691 amino acids and their sequence identity is 69% with very similar, but not identical, three dimensional structures [Metz-Boutigue M H, Jolles J, Mazurier J, Schoentgen F, Legrand D, Spik G, Montreuil J, Jolles P. Human lactotransferrin: amino acid sequence and structural comparisons with other transferrins. Eur J Biochem 145; 659 (1984)]. In human lactoferrin ~20% of the amino acids are composed of aspartic and glutamic acids [Querinjean P, Masson P L, Heremans J F. Molecular weight, single-chain structure and amino acid composition of human lactoferrin. Eur J Biochem 20; 420 (1971)]. These residues present a high concentration of carboxylic acid groups to lactoferrin. Each lactoferrin comprises of two homologous lobes, called the N and C-lobes referring to the N-terminal and C-terminal part of the molecule respectively. Each lobe further comprises two sub-lobes or domains which form a cleft where the ferric iron is tightly bound in synergistic cooperation with a (bi) carbonate anion. In addition to this, lactoferrin also has a highly charged N-terminal tail which has been implicated in many of its biological activities.

One of the most significant physicochemical feature of lactoferrin is its high affinity for iron. However, lactoferrin also possesses pleiotropic functions independent of its iron-binding capacity which have been attributed to several factors particularly due to its ability to induce signal transduction through cell surface receptors.

Classical lactoferrin receptors (LFRs) have been identified on many cell types. Recent studies have indicated that other receptors such as low density lipoprotein receptors LRP1 and LRP2 are also involved in lactoferrin biological functions. Even though the various intracellular events following receptor binding is not completely understood, lactoferrin is shown to activate different intracellular signaling pathways [Lee S, Pyo C, Hahm A H, Kim J, Choi Sy. Iron-saturated lactoferrin stimulates cell cycle progression through P13K/AKT pathway. Molecules and Cells, 28, 37 (2009)]. Functional properties also result from the interaction of its N-terminal moiety with both soluble and membrane bound molecules. In short, several unique biological functions of lactoferrin have been identified that includes anti-bacterial and anti-viral activity, regulation of cell growth and differentiation and modulation and/resolution of inflammation, induction of apoptosis in solid tumor cell lines and prevention of apoptosis in many normal cell types.

Lactoferrin has anti-inflammatory properties. The timing and its abundant release from polymorphonuclear cells during inflammation suggests the function of lactoferrin might be predominantly one of negative feedback regulation to prevent uncontrolled inflammation [van der Velden W J F M, Blijlevens N M A , Donnelly J P. The potential role of lactoferrin and derivatives in the management of infectious and inflammatory complications of hematology patients receiving a hematopoietic stem cell transplantation. Transpl infect Dis 10: 80 (2008)]. Indeed, several studies have supported this by showing lactoferrin to possess anti-inflammatory activity and exhibit inhibition of the effector phase of adaptive cellular immune reactions. Therefore, lactoferrin seems to be a part of the innate defenses attenuating inflammation and adaptive cellular immune responses, thereby promoting resolution and repair [Dhennin-Duthille J, Masson M, Damines E, Fillebeen C, Spik G, Mazurier J. Lactoferrin upregulates the expression of CD4 antigen through the stimulation of the mitogen-activated protein kinase in the human lymphoblastic T Jurkat cell line. J cell Biochem 79: 583 (2000)].

A major anti-inflammatory activity of LF is related to the scavenging of free iron which accumulates in inflamed tissues and catalyses the production of tissue-toxic hydroxyl radicals [Legrend D, Elass E, Pierce A, Mazurier J. Lactoferrin and host defence: an overview of its immuno-modulating and anti-inflammatory properties. Biometals, 17: 225 (2004]. The binding of LF to lipopolysaccharides (LPS) through the cationic N-terminal end prevents priming of neutrophils, leading to an inhibition of superoxide anion production and subsequent inflammation.

The presence of LF also leads to an altered expression of pro-inflammatory cytokines such as TNF-$\alpha$, IL-1$\beta$, IL-6 and IL-8 [Legrend D, Elass E, Carpentier M, Mazurier J. Lactoferrin: a modulator of immune and inflammatory responses. Cell Mol Life Sci 62: 2549 (2005)]. In short, at the cellular level, LF modulates the migration, maturation and function of immune cells. At the molecular level and in addition to iron binding, interactions of lactoferrin with a plethora of compounds account for its modulatory properties.

In addition, LF has bacteriostatic and bactericidal activity against Gram positive and Gram-negative bacteria. Binding of LF to lipopolysaccharides (LPS) is considered as one of the mode of antibacterial action [Majerle A, Kidric J, Jerala R. Enhancement of antibacterial and lipopolysaccharide binding activities of a human lactoferrin peptide fragment by the addition of acyl chain. J Antimicrobial Chemotherapy 10.1093/1 (2003)]. The binding of the N-terminal region of LF to the cell walls of fungi and bacteria also causes membrane perturbation and leakage of intracellular components [Arnold, R. R., Cole, M. F. & McGhee, J. R. A bactericidal effect for human lactoferrin. Science 197, 263 (1977); Bortner, C. A., Miller, R. D. & Arnold, R. R. Bactericidal effect of lactoferrin on Legionella pneumophila. Infection and Immunity 51, 373 (1986); Kalmar, J. R. & Arnold, R. R. Killing of Actinobacillus actinomycetemcomitans by human lactoferrin. Infection and Immunity 56, 2552 (1988)].

Recently, some studies indicate that LF promotes proliferation and differentiation of osteoblasts and inhibits osteoclast-mediated bone resorption [Cornish J J, Palmano K, Callon K E, Watson M, Lin J M, Valenti P, Naot D, Grey A B, Reid L R. Lactoferrin and bone: structure activity relationships. Biochem Cell Biol 84: 297 (2006); Cornish J. Lactoferrin promotes bone growth Biometals 17: 331 (2004); Cornish J, Callon K E, Naot D, Palmano K P, et al, Lactoferrin is a potent regulator of bone cell activity and increases bone formation in vivo. Endocrinology, 145: 4366 (2004); Naot D, Grey A, Reid I R, Cornish J. Lactoferrin—A novel bone growth factor. Clinical Medicine and Research. 3: 93 (2005)].

Lactoferrin is expressed in the embryo and presumed to play a role in the development and function of chondrocytes and osteoblasts in the fetal skeleton [Ward P P, Mendoza-meneses M, Mulac-Jericevic B, Cunningham G A, Saucedo-Cardenas O, Teng C T, Conneely O M. Restricted Spatiotemproal expression of lactoferrin during murine embryonic development. Endocrinology. 140: 1852 (1999)].

The growth stimulating effect of LF on osteoblast cells are complemented by its capacity to virtually halt osteoblast apoptosis. The effect has been found to be far greater than classic osteoblast growth factors such as IGF-1 or TGF-$\beta$. Further, lactoferrin is shown to have a profound effect on osteoblast maturation, promoting bone matrix deposition and mineralization [Cornish J, Callon K E, Naot D, Palmano K P, et al, Lactoferrin is a potent regulator of bone cell activity and increases bone formation in vivo. Endocrinology, 145: 4366 (2004); Naot D, Grey A, Reid I R, Cornish J. Lactoferrin—A novel bone growth factor. Clinical Medicine and Research. 3: 93 (2005); Takayama Y, Mizumachi K. Effect of lactoferrin-embedded collagen membrane on osteogenic differentiation of human osteoblast like cells. J Biosci Enf. 107: 191 (2009)].

A recent study using a subclone of C2 myoblast cells demonstrated that lactoferrin can significantly enhance ALPase activity, the osteoblastic and chondrogenic mRNA expression of Runx2, osteocalcin and Sox9 and the synthesis of Runx2 and Sox9 in pluripotent mesenchymal stem cells. Thus, lactoferrin accelerates the differentiation towards osteogenic and chondrogenic lineages where as it inhibits the myogenic and adipogenic differentiation of pluripotent mesenchymal cells [Yagi M, Suzuki N, Takayama T, Arisue M, Kodama T, Yoda Y, Otsuka K, Ito K. Effects of lactoferrin on the differentiation of pluripotent mesenchymal cells. Cell biology international 33: 283 (2009)]. This is further confirmed by a recent study using preadipocyte cells which showed that lactoferrin suppresses the adipogenic differentiation of MC3T3-G2/PA6 cells by altering the levels of the transcription factors [Yagi M, Suzuki N, Takayama T, Arisue M, Kodama T, Yoda Y, Namasaki H, Otsuka K, Ito K Lactoferrin suppress the adipogenic differentiation of MC3T3-G2/PA6 cells. J Oral Science 50: 419 (2008)]. These studies identified the bovine and human LFs as anabolic factors in skeletal tissue.

In vivo local injection of LF in adult mice resulted in increased calvarial bone growth, with significant increases in bone area and dynamic histomorphometric indices of bone formation after only five injections [Cornish J, Callon K E, Naot D, Palmano K P, et al, Lactoferrin is a potent regulator of bone cell activity and increases bone formation in vivo. Endocrinology, 145: 4366 (2004)]. The potency is further demonstrated by the fact that evidence of increased bone formation was observed on the intracranial aspect of the calvariae and on the un-injected contralateral hemicalvariae, something not seen with most other biological agents studied in this model. In summary, these studies demonstrate that lactoferrin is one of the most potent known regulators of bone mass.

It has been surprisingly demonstrated herein that cross-linked lactoferrin can support cell adhesion, cell growth, and signal transduction by cells. A key difference between LF and other osteogenic molecules such as bone morphogenic proteins (BMPs) is in the high concentrations of LF required for a significant increase in cell viability and osteogenic protein expression (e.g., alkaline phosphatase). As demonstrated herein, cell viability generally increases with increasing concentrations of LF. This is not surprising as the natural concentration of LF in human body is in the range of several μg/ml compared to ng levels in the case of BMPs. This underlines the need to introduce high concentrations of LF at the defect site for tissue repair and regeneration rather than controlled delivery of small concentrations of the protein (such as by using non-cross-linked LF, or pegylated LF). Compositions comprising non-crosslinked LF will be inadequate due to the rapid dissolution of the LF, resulting in only low concentrations of LF that are likely to be insufficient to support strong cell growth and tissue regeneration. Consequently, a desired property of a regenerative biomaterial is the maintenance of a high concentration of LF at the site of tissue regeneration for a desired period of time.

Thus, one aspect of the invention is a regenerative biomaterial which comprises, consists essentially of, or consists of cross-linked lactoferrin ("LF"). As used herein, "cross-linked lactoferrin" refers to a lactoferrin composition in which individual lactoferrin proteins within the lactoferrin composition are cross-linked to other lactoferrin proteins within the lactoferrin composition. In a particular embodiment, lactoferrin has multiple cross-linkages between lactoferrin proteins. In one embodiment, cross-linked lactoferrin comprises cross-linkages of carboxyl groups, amino groups, functionalized carboxyl groups, functionalized amino groups, or a combination thereof, of lactoferrin. Methods of producing cross-linked lactoferrin are described herein and can be prepared using standard techniques. Lactoferrin can be from any suitable source (e.g., human, bovine, or other mammalian species, recombinant, or synthetic), as will be appreciated by those skilled in the art.

In a further embodiment, the regenerative biomaterial comprises, consists essentially of, or consists of a cross-linked composite of lactoferrin and other polymers and molecules. In one embodiment, the cross-linked composite is a cross-linked solid (or gel) composite. The reaction of (multi) functionalized lactoferrins (for e.g., tyrosinated lactoferrins) with other polymers having functional groups (e.g., tyrosine groups) will result in a cross-linked gel or solid where cross-links will form between lactoferrins, between the second molecules and between lactoferrin and the second polymer and/or molecules. The cross-linked LF described herein is distinguished from lactoferrin in which the lactoferrin proteins, rather than cross-linked together at multiple sites, are attached to a separate support, matrix or chemical component such as polyethylene glycol (PEG). Such molecules (e.g., PEG) are attached to lactoferrin using a monofunctional group present in the molecule to prevent cross-linking The regenerative biomaterial as described herein is not simply a protein attached to another polymer or matrix, instead the regenerative biomaterial is a cross-linked matrix either alone or with other functionalized molecules with multiple cross-linkages in each protein, such as lactoferrin. In one embodiment, cross-linked lactoferrin is a coating on the surface of another material, e.g., microparticles, nanoparticles, ceramics, matrices, solid supports, etc.

In one embodiment, the regenerative biomaterial comprises at least, or at least about 100 ug/ml, about 200 ug/ml, about 300 ug/ml, about 400 ug/ml, about 500 ug/ml, about 600 ug/ml, about 700 ug/ml, about 800 ug/ml, about 900 ug/ml, about 1000 ug/ml, about 1250 ug/ml, about 1500 ug/ml, about 1750 ug/ml, about 2000 ug/ml, about 2250 ug/ml, about 2500 ug/ml, 2750 ug/ml, about 3000 ug/ml, about 3250 ug/ml, about 3500 ug/ml, about 3750 ug/ml, about 4000 ug/ml, about 4250 ug/ml, about 4500 ug/ml, about 4750 ug/ml, to about 5000 ug/ml, to about 10,000 ug/ml, to about 25,000 ug/ml, to about 50,000 ug/ml, or more of cross-linked lactoferrin. In one embodiment, the regenerative biomaterial comprises at least, or at least about 100 ug/ml to at least, or at least about 1000 ug/m; of cross-linked lactoferrin. As used herein, amounts expressed as "ug/ml" are interchangeable with "ug/cm$^3$", depending on whether the regenerative biomaterial is a solution, gel or a solid, as described herein and as will be appreciated by persons of skill in the art.

In one embodiment, the cross-linked lactoferrin biomaterial (also referred to herein as a "biomatrix") is a three-dimensional (3-D) structure, such as a solid or a gel.

In one embodiment, the lactoferrin is cross-linked via carboxyl (—COOH) linkages. Methods of preparing cross-linked lactoferrin are provided herein. In one embodiment, cross-linked LF is prepared by tyrosinating LF molecules using standard techniques known to those of skill in the art. Tyrosinated LF is highly soluble in water or buffer. The aqueous solution of tyrosinated LF is then chemically cross-linked using horse radish peroxidase (HRP) catalyzed oxidation of the tyrosine groups and hydrogen peroxide (HP). Tyrosinated LF in HRP forms a cross-linked LF gel as soon as it comes in contact with HP. Other methods for cross-linking LF will be appreciated by those skilled in the art. For example, standard reactions involving carboxylic acid and amine groups such as reacting lactoferrin with polymeric and low molecular weight aldehydes such as dextran dialdehyde, hyaluronic acid dialdehyde, chondroitin sulphate dialdehyde, glutaraldehyde, etc. Alternatively, lactoferrin can be modified with acrylic or methacrylic groups, thiol groups, hydrazides, amines and crosslinking the modified polymer via photo, thermal or chemical reactions.

Another aspect of the invention is a regenerative biomaterial comprising cross-linked LF and further comprising other biodegradable polymers (e.g., proteins, polysaccharides). Biodegradable polymers, both natural and synthetic, are well known in the art and include, but are not limited to, polysaccharides, proteins, peptides, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials.

Furthermore, a regenerative biomaterial as described herein can further comprise inorganic or organic composites, such as ceramics, hydroxyapatite, calcium phosphate, carbon nanotubes as well as other polymeric, metallic and ceramic nanoparticles and microparticles. Such composite materials can impart mechanical strength to the regenerative biomaterial. As will be recognized by a person skilled in the art, the mechanical strength required for the regenerative biomaterial will depend on the location of tissue regeneration needed. Consequently, mechanical strength of the regenerative biomaterial can be suitably tailored to meet the needs of the tissue to be repaired. In a further aspect of the invention, the regenerative biomaterial is suitable as a drug delivery vehicle (e.g., prodrugs, peptidomimetics, peptides, proteins, small molecules, ribozymes, etc.). The drug of choice is incorporated into the regenerative biomaterial (e.g., by cross-linking, by encapsulation, and or by attaching to the polymer using degradable links) thereby producing a regenerative biomaterial that acts as a drug delivery vehicle when implanted in vivo. In further or alternative embodiment, the regenerative biomaterial comprises cells (e.g., osteoblasts, osteoclasts, immune cells, fibroblasts, myocytes, genetically-altered cells, embryonic and adult stem cells, endothelial cells, nerve cells (e.g., cells with genetic engineering to express or not express certain molecules, such as growth factors, bone regeneration factors, etc.), or cells expanded ex vivo.

A further aspect of the invention is a method of effecting musculoskeletal tissue repair or regeneration in a subject. The method comprises contacting the musculoskeletal defect or area needing musculoskeletal repair or regeneration with a regenerative biomaterial as described herein. Thus, in one embodiment is a method of performing a musculoskeletal tissue repair or regeneration surgery on a patient whereby the area of the musculoskeletal tissue in need of repair or regeneration is accessed and cleaned, preferably using minimally invasive techniques. The regenerative biomaterial as described herein is inserted and positioned in the appropriate area of the musculoskeletal tissue in need of repair or regeneration, and the incision is surgically closed.

In another aspect of the invention is a radio-opaque cross-linked lactoferrin. As used herein, a "radio-opaque" lactoferrin is X-ray opaque. Such a matrix is useful for clinicians and surgeons to visualize the position of the matrix during surgery. A radio-opaque cross-linked lactoferrin comprises cross-linked lactoferrin as described herein, and further comprises one or more X-ray contrast agents. In one embodiment, the one or more X-ray contrast agents is a radio-opaque salt such as barium salt, or radio-opaque nanoparticles such as metallic, semiconductor, nonmetallic nanoparticles, or a combination thereof. In another embodiment, the lactoferrin is chemically conjugated to one or more radio-opaque groups such as aromatic iodides to lactoferrin molecules. The radio-opaque lactoferrin is then cross-linked. Alternatively, lactoferrin is first cross-linked, and then chemically conjugated to one or more radio-opaque groups.

EXEMPLIFICATION

Example 1

Demonstration of the Effect of Lactoferrin Concentration and the Source of Lactoferrin on its Biological Activity Using Human Mesenchymal Stem Cells Mitogenic Effect of LF:

Cell studies were performed to evaluate the mitogenic effect of bovine and human lactoferrin using passage -3 human mesenchymal stem cells. Even though there are marked similarities in the structure and functions of bovine and human lactoferrins there are some significant differences also. The composition and three dimensional structure of human lactoferrin are slightly different from bovine lactoferrin and the most significant functional difference is that bovine lactoferrin binds iron more weakly than human lactoferrin. Since iron plays an important role in the biological functions of lactoferrin, they are expected to show some differences in their biological properties [Masson P L, Heremans J F. Lactoferrin in milk from different species. Comp Biochem Physiol B. 39: 316 (1971); Spik G, Coddeville B, Mazurier J, Bourne Y, Cambillaut C & Montreuil J Primary and three-dimensional structure of lactotransferrin (lactoferrin) glycans. Advances in Experimental Medicine and Biology 357, 21 (1994); Metz-Boutigue M H, Jolles J, Mazurier J, Schoentgen F, Legrand D, Spik G, Montreuil J, Jolles P. Human lactotransferrin: amino acid sequence and structural comparisons with other transferrins. Eur J Biochem 145; 659 (1984)]. FIGS. 1A and 1B show the mitogenic effect of bovine and human lactoferrin as a function of protein concentration. The cell viability was determined using standard MTS assay. Human lactoferrin showed an increase in cell viability as a function of concentration throughout the period of study, however in the case of bovine lactoferrin the maximum viability was achieved at a concentration of 100 µg/ml.

Significance: The data shows some of the key differences between bovine and human LF towards human stem cells and also between LF and other osteogenic or mitogenic molecules such as bone morphogenetic proteins (BMP) and transforming growth factor-β (TGF-β). One key difference being the high concentrations of LF required to impart significant mitogenic effect (≥100 µg/ml) compared to BMP or TGF-β, which are required only at ng levels. It is not surprising since the natural concentration of LF in human body is in the range of µgs/ml. This underlines the need to introduce high concentrations of LF at the defect site for a prolonged time to impart tissue regeneration. Another advantage of LF is its low cost compared to bioactive proteins such as BMP and TGF-β. A still further of LF advantage is the slow increase in favorable property development with LF concentration. This is favorable for modulating the bioactivity of the biomatrix while avoiding unfavorable side effects, such as normally observed with highly inductive molecules such as BMPs.

The high cell and /tissue specificity of LF is evident from a study wherein the LF concentrations at which high viability of osteoblast and chondrocyte cells were observed showed lower macrophage viability (see Blais A, Malet A, Mikogami T, Martin-Rouas C, Tome D. Oral bovine lactoferrin improves bone status of ovariectomized mice. Am J Physiol Endocrinol Metab 296: E1281-1288 (2009)).

In summary, these unique properties of LF combined with the fact that a high concentration of the protein is required for a prolonged time to impart biological activity, and comparatively lower cost of the protein evidence the advantages of developing a biomaterial from LF as a practical approach to utilize the unique bioactivities of this molecule.

Example 2

Injectable Formulation from LF

An injectable matrix from LF was developed by utilizing the high concentration of carboxylic acid groups in the LF molecule. The injectable biomaterial design involved tyrosinating LF molecules and imparting chemical cross-linking of the protein via horse radish peroxidase (HRP) catalyzed oxidation of tyrosine groups using hydrogen peroxide (HP). The feasibility of tyrosinating LF using standard carbodiimide chemistry in the presence of tyramine was demonstrated.

Oxidative cross-linking of tyrosinated lactoferrin: The oxidation of tyramine, tyrosine and related compounds with peroxidase is a well known method [Gross A J, Sizer I W. The oxidation of tyramine, tyrosine and related compounds by peroxidase. Journal of Biological Chemistry, 234: 16711 (1959)]. As described herein, enzymatic oxidation of tyrosine groups in lactoferrin in the presence of hydrogen peroxide was used to develop an injectable gel formulation. Even though ~20 residues/molecule of tyrosine is present in LF, the native lactoferrin solution in water did not form a solid gel in the presence of horse radish peroxidase and hydrogen peroxide. So, additional tyrosine groups were incorporated in the molecule by utilizing the carboxylic groups of the protein to introduce more tyrosine groups via tyramine-carboxylic acid coupling. Briefly, lactoferrin was reacted with different concentrations of tyramine hydrochloride in MES buffer (2-(N-morpholino)ethanesulfonic acid) in the presence of different concentrations of water soluble carbodiimide and N-hydroxysuccinimide. The reaction was allowed to proceed at room temperature with stirring for 24 hours protected from light. The solution was then purified by dialyzing against water for 72 hours. The solution was then lyophilized to get the tyrosine substituted lactoferrin.

The tyrosinated lactoferrin is highly soluble in water or buffer. The aqueous solution of tyrosinated lactoferrin was mixed with different concentrations of horse radish peroxidase. The solution forms a gel as soon as it comes in contact with hydrogen peroxide.

In one example, the injectable matrix was prepared by dissolving tyrosinated lactoferrin (modified lactoferrin) in dilute HRP solution (10 U/ml) and mixed with dilute HP (0.33%). Depending on the concentration of lactoferrin, matrices with different water contents can be prepared. FIGS. 2A and 2B shows the photograph of lactoferrin solutions (FIG. 2A) and lactoferrin matrices (FIG. 2B) prepared using the HRP-HP method.

Figure 12:
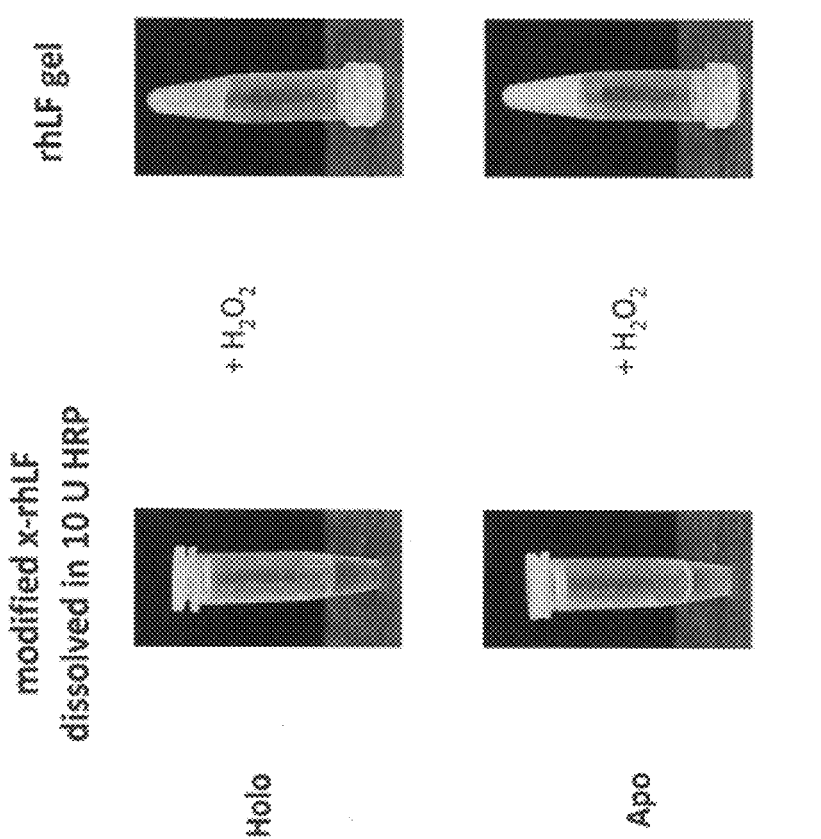
FIG. 12 demonstrates gelation of recombinant human lactoferrin (rhLf) with different iron content: holo (iron saturated) and apo (devoid of iron).

In a further example, the feasibility of developing injectable lactoferrin compositions from different lactoferrins sources (e.g., bovine and human milk lactoferrins) as well as recombinant human lactoferrins (rhLfs) has been tested. Additionally, the feasibility of gel formation with lactoferrins of different iron contents, e.g., holo (iron saturated) and apo (devoid of iron) has been demonstrated. FIG. 12 shows the gelation of holo- and apo-lactoferrins.

Figures 13A, 13B:
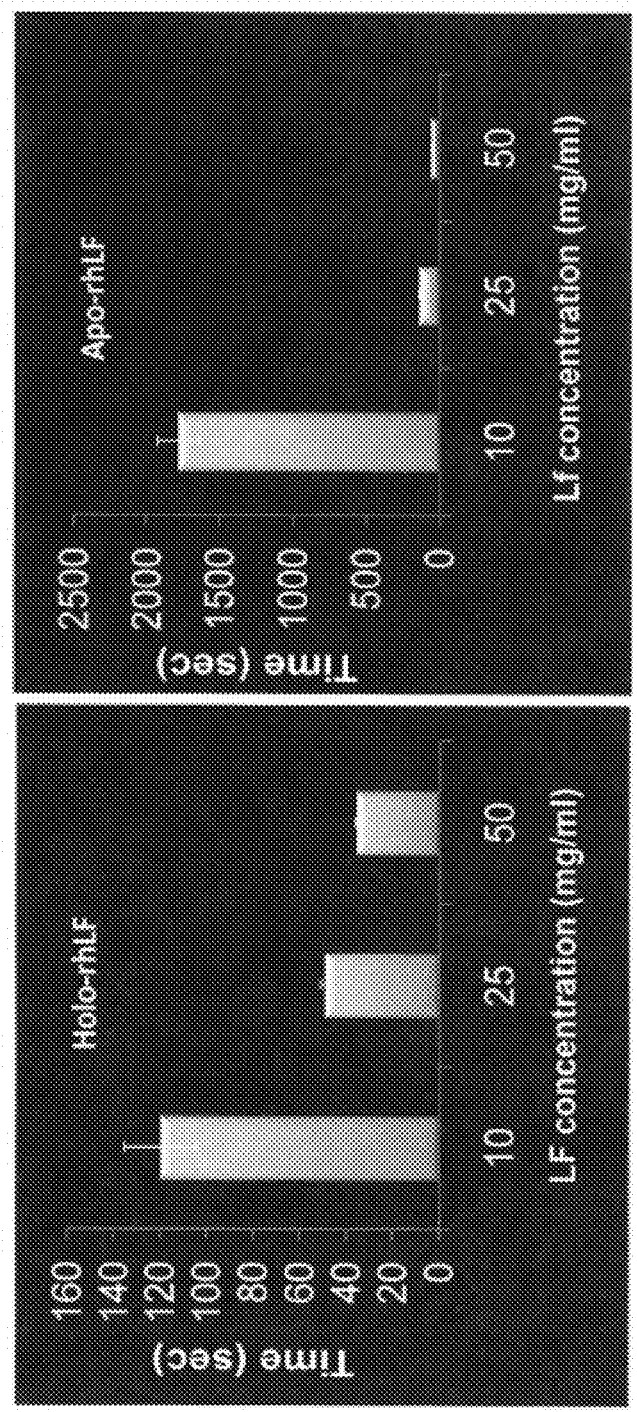
FIGS. 13A-13B are graphs demonstrating the effect of rhLf concentration on gelation time.
Figures 14A, 14B, 14C, 14D, 14E, 14F, 14G, 14H, 14I:
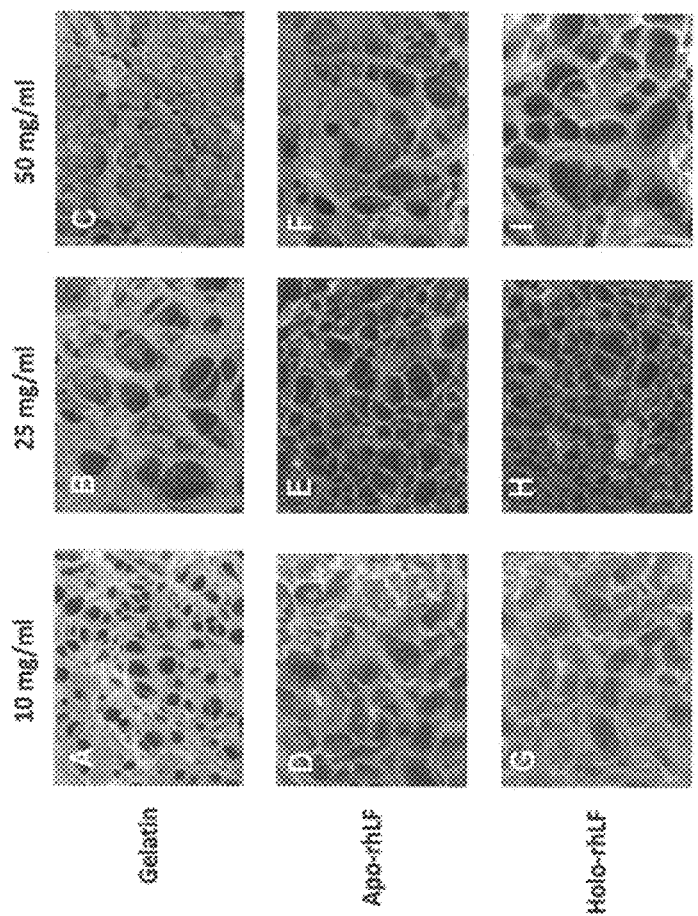
FIGS. 14A-14I are photographs showing the gel morphology of different concentrations of lactoferrins compared to gelatin gels.

The gelation time can be affected by different parameters such as the lactoferrin, hydrogen peroxide and horse radish peroxidase concentration. Therefore the gelling time can be varied from less than about a minute to about a few hours by varying the different reaction parameters. FIGS. 13A and 13B graph the effect of the indicated rhLf concentrations on the gelation time for both holo- and apo-forms of lactoferrin in 100 µl of 10 U HRP+0.75 µl of 0.25% $H_2O_2$.

Gel morphology was also studied. The cross-linked matrices of the present invention present an interconnected porous microstructure highly suitable for cell encapsulation (see FIGS. 14D-14I). As a control, gelatin gels were prepared in a similar way (gelatin reacted with tyramine and modified gelatin dissolved in HRP and treated with hydrogen peroxide) (see FIGS. 14A-14C). As can be seen in FIGS. 14D-14I, holo- and apo-lactoferrins present an open porous structure. Method: briefly, modified lactoferrins or modified gelatin were dissolved in 20 U HRP and mixed with 1 uL of 0.33% hydrogen peroxide to form the gels. The gels were then flash frozen by dipping in liquid nitrogen and lyophilized. The lyophilized gels were observed using scanning electron microscope.

Significance: The study demonstrated the feasibility of developing injectable formulations using tyrosinated lactoferrin. One of the unique properties of lactoferrin observed was the effect of lactoferrin concentration on the biological properties (see Example 1). This requires the development of an injectable system where the concentration of LF needs to be controlled to obtain the appropriate biological effect depending on the application. A composite approach in which other degradable polymers and/or degradable molecules such as peptides are incorporated might be appropriate to develop biomaterials with the required concentration of LF without compromising the physical and mechanical properties. Composite regenerative biomaterials are useful for biomaterial property modulation. For example, composite regenerative biomaterials can be developed with a solid matrix comprising lactoferrin and another polymer that acts as a bulking agent. Since the biological activity of lactoferrin is concentration dependent, this strategy permits the modulation of the biological activity of the regenerative biomaterial by varying the concentration of lactoferrin with the amount of the bulking agent. Furthermore, composite regenerative biomaterials can assist in the in vivo degradation of the regenerative biomaterials. For example, incorporating degradable units (either as other degradable polymers or degradable fragments) in the regenerative biomaterial will assist in the disintegration of the regenerative biomaterial after the required time period (time can be modulated by varying the concentration and type of the additive in the composite) and thereby assisting in the complete removal (e.g., by degradation, absorption, etc.) from the site of injection. These requirements depends on the application, so having different options will significantly increase the versatility of the matrix. The tyrosinated lactoferrin used to develop injectable composites with appropriate concentrations of LF by mixing it with other biocompatible and biodegradable tyrosinated polymers permits a mild method for tissue regeneration that is physiologically acceptable (e.g., physiological temperature, pH, ionic content etc.) and uses minimally invasive procedures.

Example 3

Bioactivity of Modified Lactoferrin

As demonstrated above, synthetic injectable compositions based on LF were developed. Described herein is the evaluation of he biological activity of the modified polymer. FIG. 3 demonstrates the viability of human mesenchymal stem cells on tyrosinated lactoferrin film prepared by HRP-HP oxidation (as described above). As can be seen in FIG. 3, the biomaterial film supported the adhesion and proliferation of human mesenchymal stem cells (green indicates live cells and red indicates dead cells).

Figure 15:
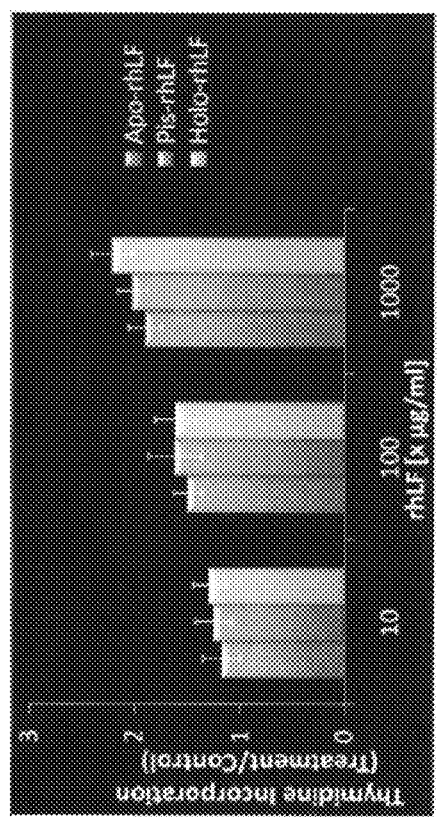
FIG. 15 is a graph showing the effect of recombinant human lactoferrin with different iron concentrations (holo, partial and apo) on MC3T3-E1 cell proliferation after 24 hours stimulation measured by thymidine incorporation. Data is expressed relative to control and asterices represent statistical significance relative to control.

The effect of lactoferrins of different iron concentrations towards preosteoblastic cell lines (MC3T3-E1) was also tested. The studies showed that irrespective of the iron concentration, the lactoferrins exhibit mitogenic and osteogenic activities. FIG. 15 shows the effect of recombinant human lactoferrin with different iron concentrations (holo, partial and apo) on MC3T3E1 cells proliferation after 24 hours stimulation measured by thymidine incorporation. Data is expressed relative to control and the asterisks represent statistical significance relative to control.

Figure 16:
FIG. 16 is a western blot showing the increase in phosphorylation of AKT after exposing MC3T3 E1 to lactoferrins for 15 minutes. Proteins (25 µg) were loaded on gel and immunoblotting was conducted with the indicated antibodies, in accordance with the manufacture's instructions. Anti-Tubulin blot serves as a loading control.

Another important property of lactoferrin is its ability to prevent cell apoptosis. The antiapoptotic properties of three different lactoferrins were examined by following the phosphorylation of Akt. A significant increase in phosphorylation of Akt of MC3T3 E1 cells in the presence of all the three different types of lactoferrin was found. FIG. 16 shows the increase in phosphorylation of Akt after exposing MC3T3 E1 to the indicated lactoferrins for 15 minutes. For western blot analysis, proteins (25 µg) were loaded on gel and immunoblot was conducted with the indicated antibodies, in accordance with the manufacture's instructions. The anti-tubulin blot serves as a loading control.

Figure 17:
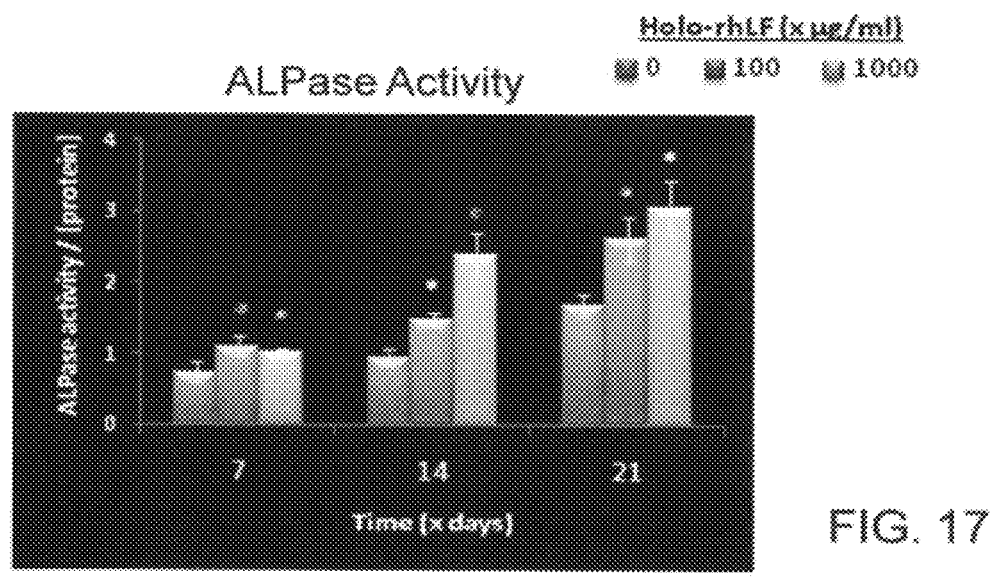
FIG. 17 is a graph showing the osteogenic activity of MC3T3-E1 cells in the presence of lactoferrin (holo-rhLF), as indicated by increase in the alkaline phosphatase activity of the cells. An increase in alkaline phosphatase activity of MC3T3-E1 cells was demonstrated after treating with hololactoferrin at different concentrations as compared to control culture (blue bar/far left bar in each time point).
Figure 18:
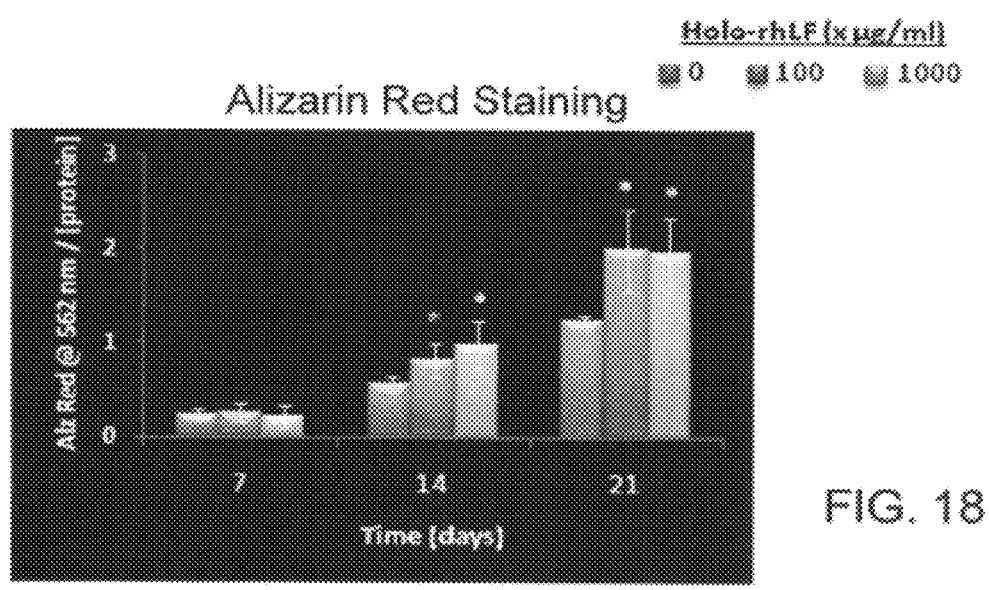
FIG. 18 is a graph showing the osteogenic activity of MC3T3-E1 cells in the presence of lactoferrin (holo-rhLF), as indicated by the increase in calcium deposition by the cells. An increase in calcium matrix deposition by MC3T3-E1 cells was demonstrated after treating with hololactoferrin at different concentrations as compared to control culture (blue bar/far left bar in each time point).

The osteogenic activity of lactoferrins was also investigated. FIGS. 17 and 18 show the osteogenic activity of the indicated lactoferrins towards MC3T3-E1 cells as indicated by increase in the alkaline phosphatase activity of the cells and the increase in calcium deposition by the cells. FIG. 17 shows the increase in alkaline phosphatase activity of MC3T3-E1 cells after treating with hololactoferrin of different concentrations as compared to control culture (blue). FIG. 18 shows the increase in calcium matrix deposition by MC3T3-E1 cells after treating with hololactoferrin of different concentrations compared to control culture (blue).

Figure 19:
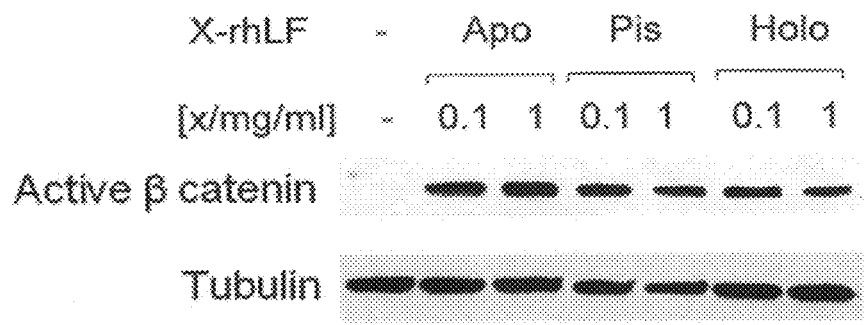
FIG. 19 is a western blot showing upregulation of osteogenic signaling molecules in cells exposed to lactoferrins of different iron concentrations. MC3T3-E1 cells were treated with the indicated amounts of lactoferrins holo, apo and partial. Treatment with all the proteins increased the accumulation of active beta-catenin which is an indication of cells going towards the osteogenic pathways. The control (no lactoferrin) indicates minimal expression of beta-catenin under the experimental conditions.

The upregulation of osteogenic signaling molecules in cells exposed to lactoferrins of different iron concentrations was also investigated. Holo, apo and partial lactoferrins were tested with MC3T3-E1 cells. As can be seen in FIG. 19 all the lactoferrins increased in the accumulation of active beta-catenin, which is an indication of cells going towards the osteogenic pathways. Minimal expression of beta-catenin is found under the experimental conditions in the absence of the test lactoferrins.

Figure 20:
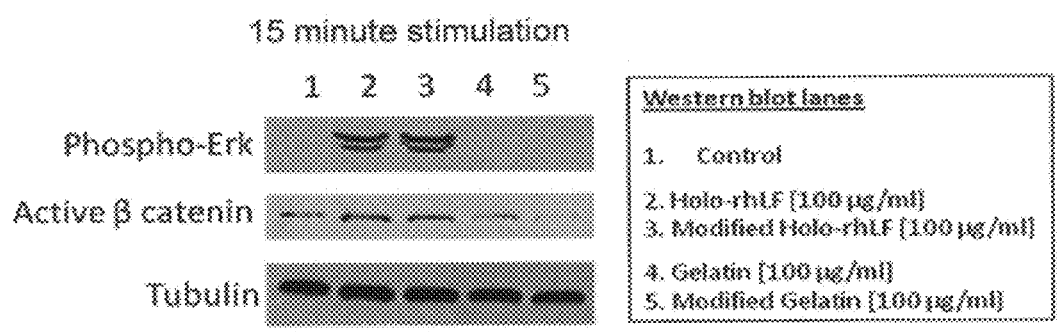
FIG. 20 is a western blot showing the phosphorylation of ERK (which indicates the ability of lactoferrin to promote cell proliferation) and the presence of active beta catenin (which indicates the ability of lactoferrins to promote osteogenesis) of cells exposed to lactoferrins and modified lactoferrins (reacted with tyramine). As illustrated by western blot, no differences in biological activities were observed between holo lactoferrin and modified holo lactoferrin. Gelatin was used as a control. The gelatin was subjected to the same reactions to prepare a modified gelatin and serve as a control.

Lactoferrins reacted with tyramine retain the biological properties of lactoferrin. Biological activity studies were performed to confirm that the reaction of tyramine with lactoferrins to form modified recombinant human lactoferrins retain these biological activities. The phosphorlation of ERK (which indicates the ability of lactoferrin to promote cell proliferation) and the presence of active beta catenin (which indicates the ability of lactoferrins to promote osteogenesis) of cells exposed to lactoferrins and modified lactoferrins (reacted with tyramine) were tested to determine if the tyramine modification changed the lactoferrin biological activity. As demonstrated in FIG. 20, no differences in biological activity was observed between holo lactoferrin and modified holo lactoferrin. Gelatin gel was used as a control: the gelatin was subjected to the same reaction as the lactoferrins to prepare modified gelatin to serve as a suitable control. For cell culture, briefly, MC3T3 cells were grown to 90% confluence in basal medium and then serum starved overnight and treated with the appropriate treatments as described above for 15 minutes.

Figure 21:
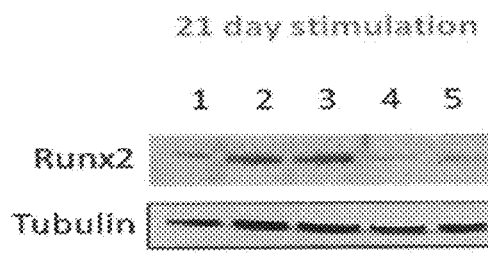
FIG. 21 is a western blot showing the expression of RunX2—a key transcription factor for osteogenic differentiation—to determine if modified lactoferrin had altered the osteogenic activity of lactoferrin. As shown, both holo lactoferrin and modified holo lactoferrin (lanes 2 and 3) showed an upregulation of RunX2 compared to control culture (lane 1) and cells treated with gelatin (lane 4) and modified gelatin (lane 5).

The expression of RunX2—a key transcription factor for osteogenic differentiation—was also tested to determine if tyramine modification altered the osteogenic activity of the lactoferrin. As shown in FIG. 21, both holo lactoferrin and modified holo lactoferrin (lanes 2&3) showed an upregulation of RunX2 compared to control culture (lane 1) and cells treated with gelatin (lane 4) and modified gelatin (lane 5). Methods: briefly, MC3T3 cells were grown to 90% confluence in basal medium and then grown in mineralization medium and treated with the appropriate treatments for 21 days.

Figures 22A, 22B, 22C, 22D, 22E, 22F, 22G, 22H:
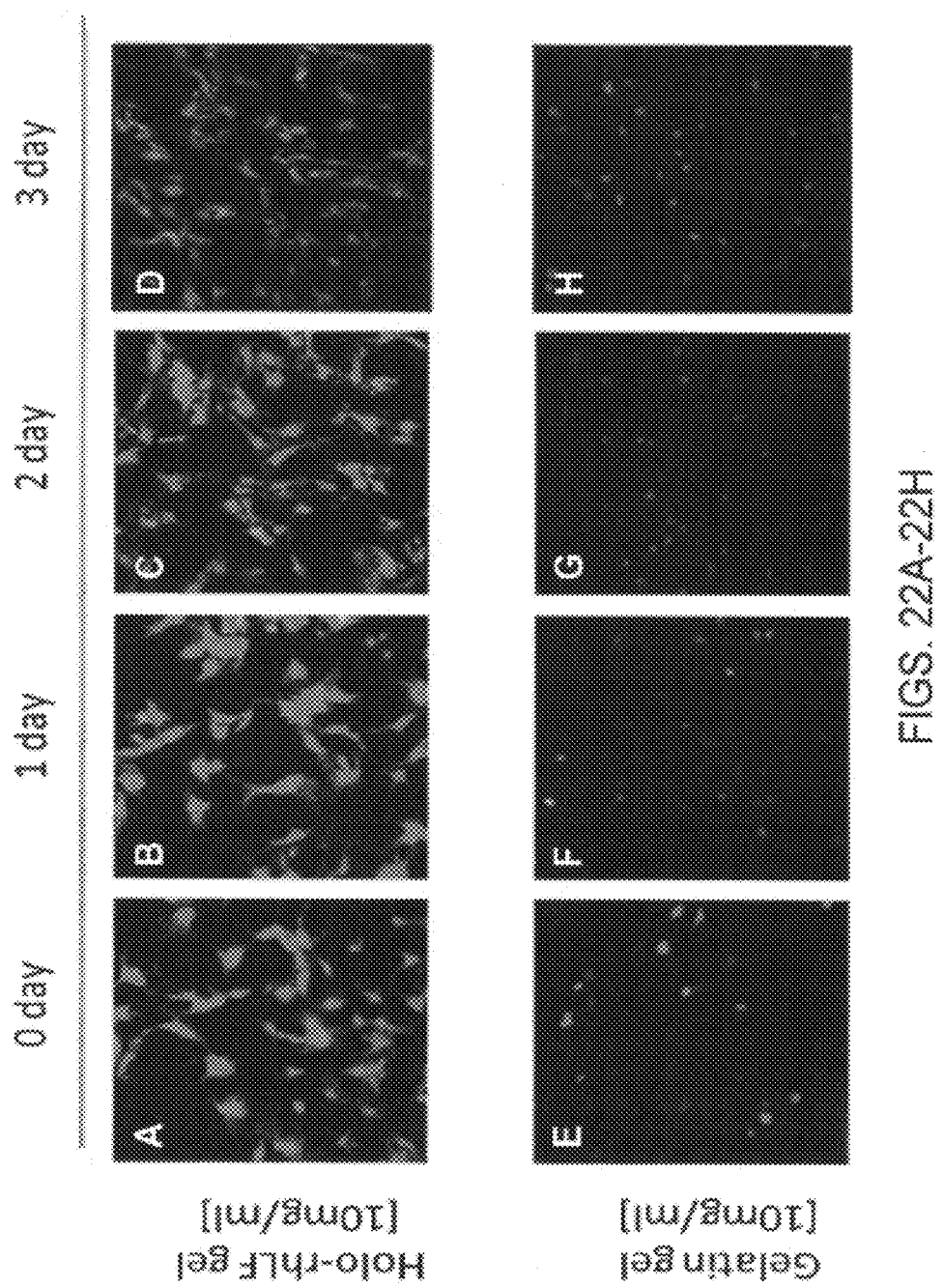
FIGS. 22A-22H is a series of photographs demonstrating the anti-apoptotic effect of lactoferrin gel compared to gelatin gel in in vitro studies using MC3T3-E1 cells. Green staining identifies viable cells; red staining identifies dead cells. MC3T3-E1 cells were encapsulated in either holo lactoferrrin gel (FIGS. 22A-22D) or gelatin gel (FIGS. 22E-22H), and grown in basal medium for 24 hours. Cells were then maintained in serum-free media to induce apoptosis and imaged using live/dead. Cells were imaged at 0 days (FIGS. 22A and 22E); 1 day (FIGS. 22B and 22F); 1 day (FIGS. 22C and 22G); and 3 days (FIGS. 22D and 22F). Upon serum starving, within 24 h significant cell death was observed for cells in the gelatin gel (FIG. 22F), whereas cells encapsulated in lactoferrin gel showed significant viability (FIG. 22B). The cells encapsulated in lactoferrin maintained it viability even up to almost 3 days when cultured in serum free media (see FIGS. 22D and 22H).

Additional studies were performed to investigate whether the biological activities described above were preserved in the injectable gel formulations. In vitro studies using MC3T3-E1 cells demonstrated excellent anti-apoptotic effect of lactoferrin gel compared to gelatin gel (using a 3D control gel). Method: briefly, 500,000 cells/ml were prepared in 100 µl of 10 mg/ml holo-rhLF gel (10 U HRP, 0.75 µl of 0.25% $H_2O_2$). Cells were encapsulated and then grown in basal medium for 24 hours. Cells were then maintained in serum free media to induce apoptosis and imaged using a live/dead assay. As shown in FIGS. 22A-22H, cells spread very well in holo lactoferrrin gel (FIGS. 22A-D), where as it had a more rounded morphology in gelatin gel after 24 h culture (FIG. 22E). Upon serum starving, within 24 h significant cell death was observed in gelatin gel (FIG. 22F), whereas cells encapsulated in lactoferrin gel showed significant viability (FIG. 22B). The cells encapsulated in lactoferrin maintained it viability even up to almost 3 days when cultured in serum free media (FIGS. 22C and 22D). Green staining shows viable cells and red staining shows dead cells in FIGS. 22A-22H.

Next the deposition of collagen I matrix by cells encapsulated in lactoferrin gel and gelatin gel was investigated. The cell nucleus was stained in red and collagen was stained in green, see FIGS. 23A and 23. Cells encapsulated in lactoferrin showed a significant increase in collagen matrix deposition (see FIG. 23B) compared to cells encapsulated in gelatin (see FIG. 23A).

To confirm that the cells encapsulated in the lactoferrin gel still retained their ability to increase cell proliferation, the encapsulated cells were stained with Ki67 after 48 h. Ki67 is a marker for multiplying cells. Method: briefly, 500,000 cells/ml were encapsulated in 100 µl of 10 mg/ml holo-rhLF gel (10 U HRP, 0.75 µl of 0.25% $H_2O_2$) and 100 µl of 10 mg/ml gelatin gel (10 U HRP, 7.5 µl of 0.025% H2O2). Cell culture was maintained in basal medium for 2 days. Immunofluorescence: secondary antibodies were labeled with FITC (green); Propidium Iodide nuclear stain (red). Cell nucleus was stained in red and multiplying cells were stained in green. As shown in FIGS. 24A and 24B, a significant number of multiplying cells after 48 h in lactoferrin gel was observed (FIG. 24B) as compared to control gelatin gel (FIG. 24A).

The ability of lactoferrin gel to phosphorylate ERK was also tested, similar to the demonstration with soluble lactoferrin discussed above. Methods: briefly, 500,000 cells/ml were encapsulated in 100 μl of 10 mg/ml holo-rhLF gel (10 U HRP, 0.75 μl of 0.25% H2O2) and 100 μl of 10 mg/ml gelatin gel (10 U HRP, 7.5 μl of 0.025% H2O2). Cell culture was maintained in basal medium for 2 days. Immunofluorescence: secondary antibodies were labeled with FITC (green); Propidium Iodide nuclear stain (red). Green fluorescence indicates the presence of phosphorylated ERK which plays a very important role on cell proliferation and osteogenic differentiation. Results demonstrate that lactoferrin gel induced significant phosphorylation of ERK as compared to cells encapsulated in gelatin gel (compare FIG. 25B with FIG. 25A, respectively).

Immunofluorescent assays to detect the phosphorylation of AKT (an indicator of the activation of antiapoptotic pathways in cells), was also tested. Cells encapsulated in gelatin gel or lactoferrin gel were stained for p-AKT. Methods: briefly, 500,000 cells/ml were encapsulated in 100 μl of 10 mg/ml holo-rhLF gel (10 U HRP, 0.75 μl of 0.25% $H_2O_2$) and 100 μl of 10 mg/ml gelatin gel (10 U HRP, 7.5 μl of 0.025% $H_2O_2$). Cell culture was maintained in basal medium for 2 days. Immunofluorescence: secondary antibodies were labeled with FITC (green); Propidium Iodide nuclear stain (red). As shown in FIG. 26B, the lactoferrin gel shows significant expression (indicated in green) of phosphoAKT compared to gelatin gel control (FIG. 26A), confirming our previous study.

In addition, the activation of beta-catenin in cells by lactoferrin gel was also investigated. Method: briefly, 500,000 cells/ml were encapsulated in 100 μl of 10 mg/ml holo-rhLF gel (10 U HRP, 0.75 μl of 0.25% H2O2) and 100 μl of 10 mg/ml gelatin gel (10 U HRP, 7.5 μl of 0.025% H2O2). Cell culture was maintained in basal medium for 2 days. Immunofluorescence: secondary antibodies were labeled with FITC (green); Propidium Iodide nuclear stain (red). FIGS. 27A and 27B shows the significant presence of active beta-catenin in cells encapsulated in lactoferrin gel (FIG. 27B) indicating the gel osteogenic activity as compared with cells encapsulated in control gelatin gel (FIG. 27A).

Significance: As demonstrated herein, cross-linking LF as described herein does not appear to affect the bioactivities of lactoferrin.

Example 4

Cells Seeded on Lactoferrin Based Gels of Different Concentrations (see FIGS. 3-6)

MC3T3-E1 pre-ostoeblastic cells were seeded on lactoferrin based gels as soon as it was prepared as described above (to prevent gel drying). Various lactoferrin concentrations were tested: 100 ug; 200 ug; and 1000 ug. Briefly, tyrosinated lactoferrin was prepared by reacting partially iron saturated lactoferrin (Sigma Aldrich) with tyramine in the presence of water soluble carbodiimide and N-hydroxysuccinimide in MES buffer for 24 h at room temperature. Incubation times and temperatures can be varied, as will be appreciated by those of skill in the art. For example, temperatures can range from at least, or about 4° C. to at least, or about 37° C. Incubation times can range from at least, or about 30 min to at least, or about 48 h, or more.

The tyrosinated lactoferrin was purified by dialysis for 2 days and lyophilized. The tyrosinated lactoferrin was dissolved in a solution of 10 U horseradish peroxide in phosphate buffer. Different concentrations of tyrosinated LF in HRP solution was mixed with 0.33 % hydrogen peroxide solution and 2004 of the solutions were placed in TCP. Quickly after gelation, 50,000 MC3T3-E1 cells were seeded on top of the wet gels. 1 mL of fresh media was added and cultured for different periods of time. The cells were stained with live/dead fluorescent staining using a two color assay that simultaneously stain live and dead cells. Live cells have intracellular esterases that convert non-fluorescent, cell-permeable calcein acetoxymethyl (calcein AM) to the intensely fluorescent calcein (green). Cleaved calcein is retained within cells. Dead cells have damaged membranes; the ethidium homodimer-1 (EthD-1) enters damaged cells and is fluorescent when bound to nucleic acids. EthD-1 produces a bright red fluorescence in damaged or dead cells. Thus, more green staining means more viable cells. The assay demonstrates the presence of well spread viable cells in/on the matrix. The optical photomicrographs of the samples are shown for comparison.

Interestingly, the cells grew unique patterns on the gel depending on the concentration of the lactoferrin solution used to prepare the gel.

Example 5

MC3T3 Cells Cultured on Tissue Culture Polystyrene Dishes in the Presence of 100 ug/ml, 200 ug/ml and 1000 ug/ml of Lactoferrin Added to the Media (see FIGS. 7A-7C)

In contrast to MC3T3 cells cultured on lactoferrin based gels described in Example 4, MC3T3 cells cultured on polystyrene dishes with media supplemented with 100 ug/ml, 200 ug/ml and 1000 ug/ml of lactoferrin demonstrate a decrease in cell number as lactoferrin concentration in the media increases from 100-1000 ug/ml (compare FIG. 7A (100 ug/ml) with FIG. 7B (200 ug/ml) with FIG. 7C (1000 ug/ml).

Example 6

Figure 8:
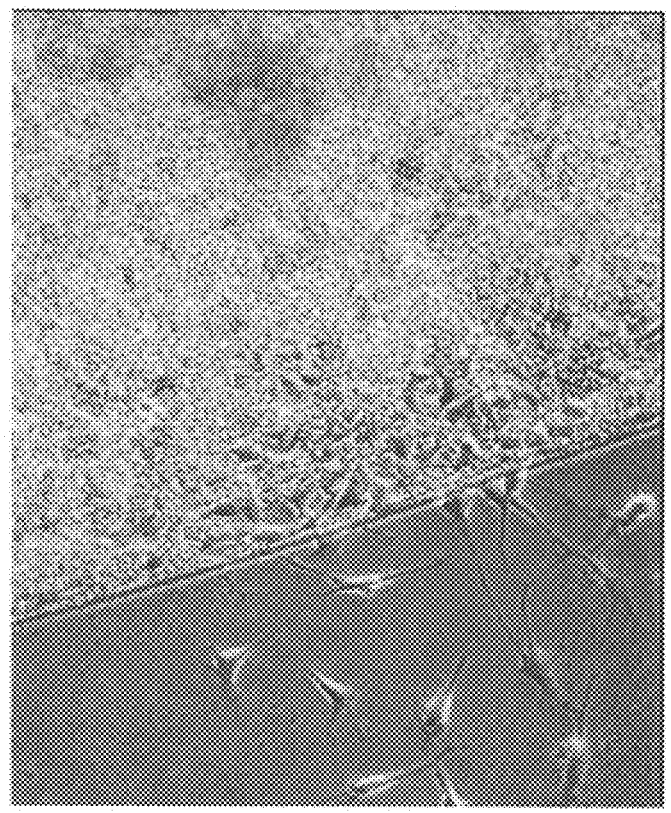
FIG. 8 is a photograph of pre-osteoblast cells (MC3T3) encapsulated inside a lactoferrin biomatrix after 7 days in culture. Briefly, tyrosinated lactoferrin was prepared by reacting partially iron saturated bovine lactoferrin (Sigma Aldrich) with tyramine in the presence of water soluble carbodiimide and N-hydroxysuccinimide in MES buffer for 24 h at room temperature. The tyrosinated lactoferrin was purified by dialysis for 2 days and lyophilized. The tyrosinated lactoferrin was dissolved in a solution of 10 U horse radish peroxidase (HRP) in phosphate buffer. As will be understood by persons of skill in the art, a suitable range of HRP is at least, or about 10-100 U/mL. The 100 µL of the solution (with 100 µg LF) was mixed with 0.33% hydrogen peroxide solution. As will be understood by persons of skill in the art, the hydrogen peroxide solution can be any suitable range, e.g., at least, or about 0.01-30%. MC3T3-E1 cells were added to the solution, mixed well and plated in a 6 well tissue culture polystyrene plate and allowed to gel. Fresh media was then added and the cells were then cultured for 7 days at 37° C.

Encapsulation of Cells in Lactoferrin Biomatrix (see FIG. 8)

Cells were encapsulated in lactoferrin gel to demonstrate biocompatibility of the gel and the gelation process with live cells. Briefly, tyrosinated lactoferrin was prepared by reacting partially iron saturated lactoferrin (Sigma Aldrich) with tyramine in the presence of water soluble carbodiimide and N-hydroxysuccinimide in MES buffer for 24 h at room temperature. The tyrosinated lactoferrin was purified by dialysis for 2 days and lyophilized. The tyrosinated lactoferrin was dissolved in a solution of 10 U horseradish peroxide in phosphate buffer The 100 ∞L of the solution (with 100 μg LF) was mixed with 0.33% hydrogen peroxide solution. MC3T3-E1 cells (100,000 cells) were added to the solution, mixed well and plated in a 6 well tissue culture polystyrene plate and allowed to gel. In this way cells are encapsulated within the gel rather than on top as described in Example 5. Fresh media was then added and the cells were then cultured for 7 days at 37° C.

Significance: Cells present during the gelation process are not adversely affected by the process, indicating the suitability of the composition for in situ and/or in vivo applications.

Example 7

Figure 9A:
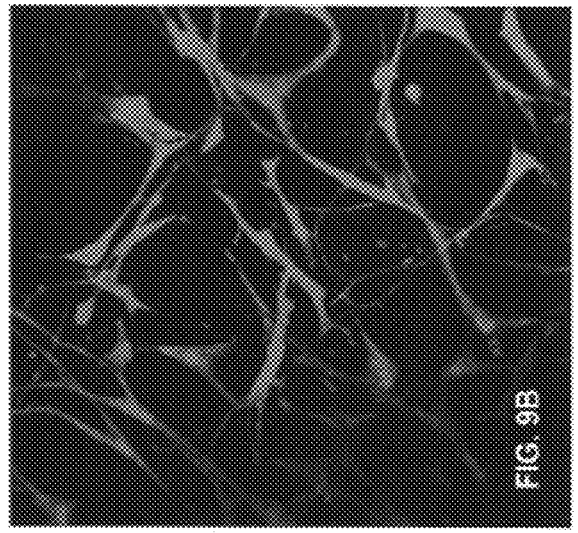
FIGS. 9A-9B are confocal images of pre-osteoblast cells (MC3T3-E1 cells).
Figure 9B:
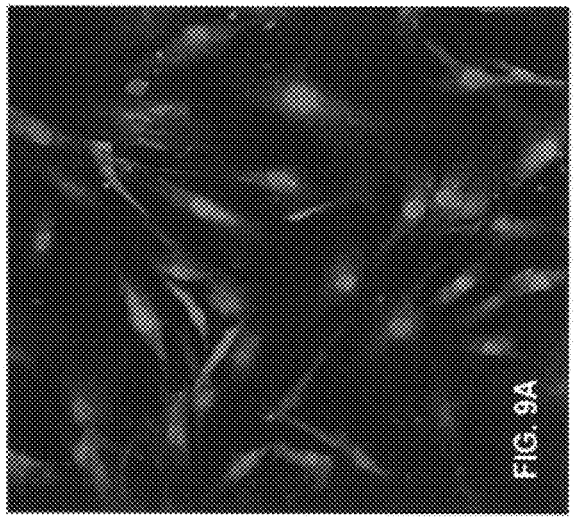
Figures 10A, 10B:
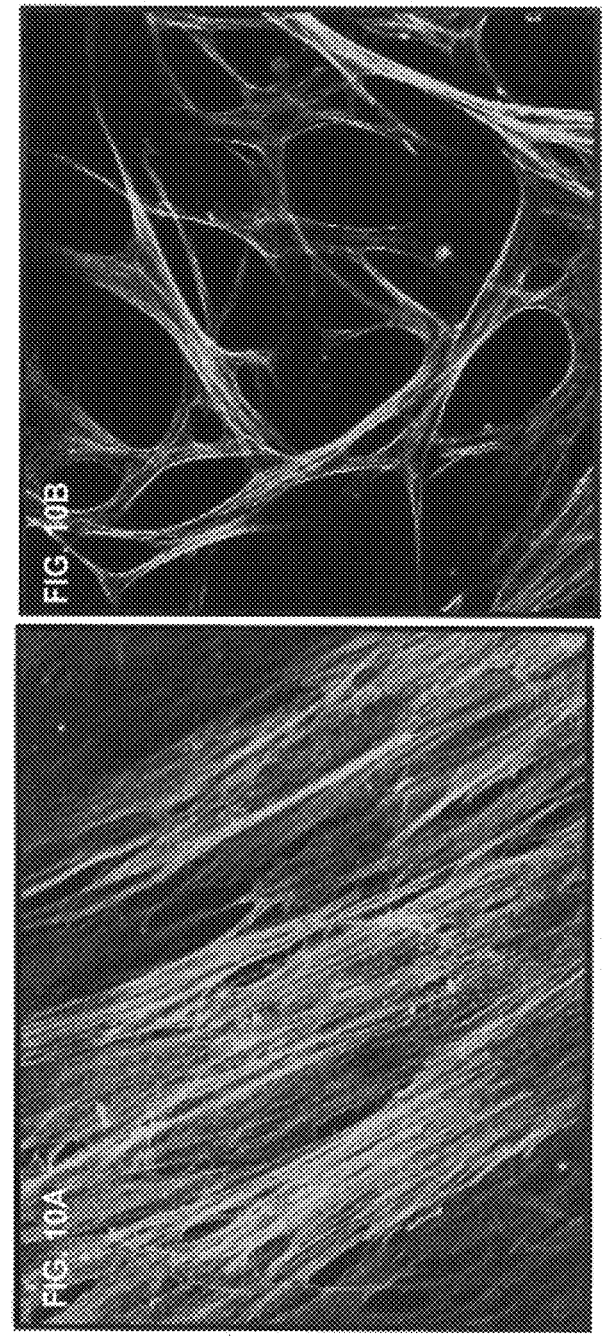
FIGS. 10A-10B are confocal images of human mesenchymal stem cells stained for actin filament orientation indicating cell morphology.
Figure 11A:
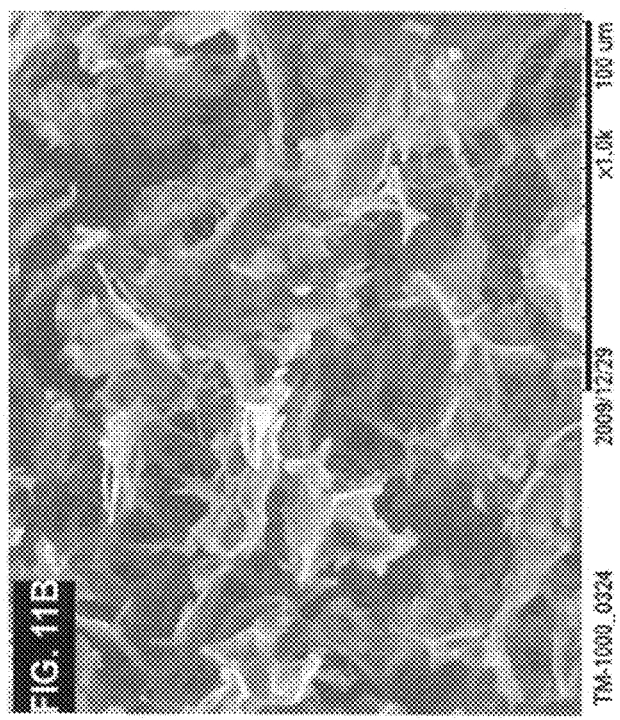
FIGS. 11A-11B are scanning electron micrographs of freeze-dried and lyophilized lactoferrin gels at a concentration of 30,000 µg/ml showing the morphology of the dried gels.
Figure 11B:
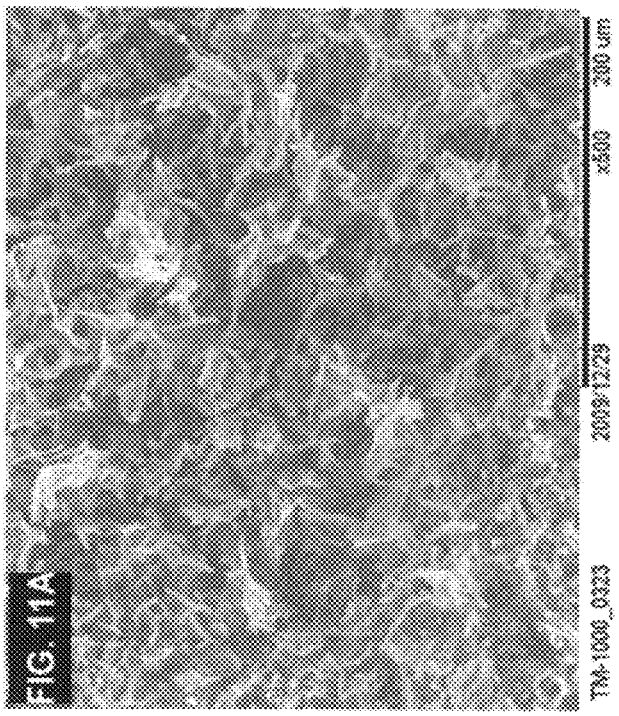

Demonstration of the Viability of MC3T3-T1 Cells and Cytoskeletal Organization of Human Mesenchymal Stem Cells Encapsulated in Lactoferrin Biomatrix (see FIGS. 9 and 10)

MC3T3-E1 cells and human mesenchymal stem cells (50,000 cells) were added to 200 μL of the solution, mixed well and plated in a glass bottomed dish suitable for confocal microscopic imaging and allowed to gel. Fresh media was then added to the dish and the cells were then cultured for 3 days at 37° C. At the end of the experiment, the media was removed and the live dead staining solution was added and incubated for 10 min. The cells were then viewed using a confocal microscope. For actin staining, instead of live-dead stain an actin stain was added and allowed to develop before imaging.

Significance:—MC3T3-E1 cell and human mesenchymal stem cell are not adversely affected by the gelation process indicating its suitability for in situ and/or in vivo applications. The live dead experiment show the viability of the cells within the matrix (which is approximately similar to TCP) and the actin stain demonstrates the cytoskeletal reorientation of the cells in the matrix (which is significantly different from the cells on TCP; the gel allowed the 3D arrangement of the encapsulated cells).

Example 8

Radio-opaque Cross-linked Lactoferrin

Different methods can be used to make radio-opaque cross-linked lactoferrin. For example, by encapsulating preformed radio-opaque salts or nano/microparticles in the injectable solution or by chemically attaching radio opaque groups to lactoferrin backbone to exhibit inherent radio opacity. Common chemical reactions involving carboxylic acid or amino functional groups in lactoferrin can be used to attach these groups. A typical example is illustrated below. Briefly, lactoferrin with tyrosine groups is prepared by reacting it with tyramine in the presence of water soluble carbodiimide and N-hydroxysuccinimide in MES buffer for 24 h at room temperature. In the case of preparing radio-opaque lactoferrins, tyramine will be fully or partially replaced by other iodine substituted tyrosine groups such as 4-Iodophenylalanine ethylester hydrochloride and/3,5-diiodotyrosine ethylester hydrochloride. This will incorporate tyrosine groups as well as iodine moiety in the polymer. The tyrosine groups will be later used to form crosslinks in the presence of HRP and HP as previously described.

Definitions

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this specification pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes minor deviations. Such deviation can be the result of inherent variation from error for the device or the method being employed to determine the value.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A regenerative biomaterial composition comprising cross-linked lactoferrin, wherein the cross-linked lactoferrin comprises cross-linkages of carboxyl groups, functionalized carboxyl groups, or a combination thereof.

2. The regenerative biomaterial composition of claim 1, wherein the cross-linked lactoferrin is tyrosinated lactoferrin.

3. The regenerative biomaterial composition of claim 1, wherein the cross-linked lactoferrin is radio-opaque.

4. The regenerative biomaterial composition of claim 1, wherein the regenerative biomaterial composition is an injectable composition.

5. The regenerative biomaterial composition of claim 4, wherein the injectable composition is a gel.

6. The regenerative biomaterial composition of claim 1, wherein the regenerative biomaterial composition further comprises a solid matrix.

7. The regenerative biomaterial composition of claim 6, wherein the solid matrix is selected from the group consisting of calcium phosphate, hydroxyapatite, ceramics, metallic nanoparticles, metallic microparticles, carbon nanotubes, and combinations thereof.

8. The regenerative biomaterial composition of claim 1, wherein the regenerative biomaterial composition comprises at least 100 ug/ml to about 50,000 ug/ml of cross-linked lactoferrin.

9. The regenerative biomaterial composition of claim 6, wherein the regenerative biomaterial composition is biodegradable in vitro and in vivo.

10. The regenerative biomaterial composition of claim 1, wherein the regenerative biomaterial composition further comprises a drug.

11. The regenerative biomaterial composition of claim 1, wherein the regenerative biomaterial composition further comprises a cell.

12. A method of preparing a regenerative biomaterial composition comprising cross-linking one or more carboxyl groups, one or more functionalized carboxyl groups, or a combination thereof, of lactoferrin to produce a cross-linked lactoferrin.

13. The method of claim 12, wherein the lactoferrin is tyrosinated lactoferrin.

14. The method of claim 12, wherein the lactoferrin is radio-opaque.

15. The method of claim 12, wherein the regenerative biomaterial composition is an injectable composition.

16. The method of claim 15, wherein the injectable composition is a gel.

17. The method of claim 12 wherein the regenerative biomaterial composition further comprises a solid matrix.

18. The method of claim 17, wherein the solid matrix is selected from the group consisting of calcium phosphate, hydroxyapatite, ceramics, carbon nanotubes, and combinations thereof.

19. The method of claim 12, wherein the regenerative biomaterial composition comprises at least 100 ug/ml to about 50,000 ug/ml of cross-linked lactoferrin.

20. A regenerative biomaterial composition produced by the method of claim 12.

21. A method of effecting musculoskeletal repair or regeneration comprising contacting the area affected by a musculoskeletal defect with a regenerative biomaterial composition comprising cross-linked lactoferrin.

22. The method of claim 21, wherein the cross-linked lactoferrin is radio-opaque.

23. The method of claim 21, wherein the cross-linked lactoferrin comprises cross-linked carboxyl groups.

24. The method of claim 21, wherein the cross-linked lactoferrin is tyrosinated lactoferrin.

25. The method of claim 21, wherein the regenerative biomaterial composition is an injectable composition.

26. The method of claim 21, wherein the regenerative biomaterial composition further comprises a solid matrix.

27. The method of claim 26, wherein the solid matrix is selected from the group consisting of calcium phosphate, hydroxyapatite, ceramics, carbon nanotubes, and combinations thereof.

28. The method of claim 21, wherein the regenerative biomaterial composition comprises at least 100 ug/ml to about 50,000 ug/ml of cross-linked lactoferrin.

29. The method of claim 21, wherein the regenerative biomaterial composition further comprises a drug.

30. The method of claim 21, wherein the regenerative biomaterial composition further comprises a cell.

* * * * *